United States Patent [19]
Gray

[11] Patent Number: 6,149,585
[45] Date of Patent: Nov. 21, 2000

[54] DIAGNOSTIC ENHANCEMENT METHOD AND APPARATUS

[75] Inventor: V. Katherine Gray, Minneapolis, Minn.

[73] Assignee: Sage Health Management Solutions, Inc., Minneapolis, Minn.

[21] Appl. No.: 09/181,294

[22] Filed: Oct. 28, 1998

[51] Int. Cl.[7] .............................. A61B 5/00; G06F 17/60
[52] U.S. Cl. ................................. 600/300; 705/2; 705/3; 128/904
[58] Field of Search ................................. 600/300–301, 600/481–486, 500–504, 544–545; 128/897–898, 904, 905, 920–925, 903, 900; 705/2–3, 4, 26–27, 35; 395/709; 707/104; 700/90; 340/286.7; 345/169

[56] References Cited

U.S. PATENT DOCUMENTS

| | | | |
|---|---|---|---|
| 4,290,114 | 9/1981 | Sinay .................................... | 364/900 |
| 4,489,387 | 12/1984 | Lamb et al. ............................ | 364/514 |
| 4,731,725 | 3/1988 | Suto et al. .............................. | 364/415 |
| 4,733,354 | 3/1988 | Potter et al. ............................ | 364/415 |
| 4,866,635 | 9/1989 | Kahn et al. ............................. | 364/513 |
| 5,025,391 | 6/1991 | Filby et al. ............................ | 364/513 |
| 5,081,598 | 1/1992 | Bellows et al. ........................ | 364/550 |
| 5,235,510 | 8/1993 | Yamada et al. ..................... | 364/413.02 |
| 5,255,187 | 10/1993 | Sorensen ................................ | 600/300 |
| 5,272,704 | 12/1993 | Tong et al. .............................. | 371/23 |
| 5,301,105 | 4/1994 | Cummings, Jr. ....................... | 600/300 |
| 5,404,292 | 4/1995 | Hendrickson .......................... | 128/920 |
| 5,469,353 | 11/1995 | Pinsky et al. ...................... | 364/413.01 |
| 5,537,590 | 7/1996 | Amado ................................... | 395/600 |
| 5,551,436 | 9/1996 | Yago ...................................... | 128/670 |
| 5,583,758 | 12/1996 | McIlroy et al. ........................ | 395/202 |
| 5,586,262 | 12/1996 | Komatsu et al. ................... | 395/200.02 |
| 5,594,638 | 1/1997 | Iliff ........................................ | 395/203 |
| 5,660,176 | 8/1997 | Iliff ........................................ | 128/630 |
| 5,779,634 | 7/1998 | Ema et al. .............................. | 128/920 |
| 5,868,669 | 2/1999 | Iliff ........................................ | 600/300 |
| 5,878,746 | 3/1999 | Lemelson et al. ..................... | 128/920 |
| 5,897,493 | 4/1999 | Brown .................................... | 600/300 |
| 5,953,704 | 9/1999 | McIlroy et al. ......................... | 705/2 |
| 5,993,386 | 11/1999 | Ericsson ................................. | 600/300 |
| 5,997,476 | 12/1999 | Brown .................................... | 600/300 |

OTHER PUBLICATIONS

Press Release, *News*, Healtheon, pp. 1–3, Jun. 18, 1996.
Polly Schneider, *Net Commerce Development Grows*, pp. 1–5, online healthcare informatics, Sep. 1997.
Robert B. Elson, *Uniting Practice Management and the CPR*, pp. 1–7, online healthcare informatics, Sep. 1997.
Press Release, James P. Bradley to Lead Abaton.com™, *New Business Venture Focused on Health Care Delivery at the Point of Care*, pp. 1–2, Abaton.com, May 5, 1997.
John Fontana, Intranets @ Work, *Health Services: Intranets: A Miracle Drug?*, pp. 1–6, Communications Week Interactive, Mar. 3, 1997.
Healtheon Company and Investor Information, *Company/Investor Info*, pp. 1–4.
Cara Cunningham, Healtheon signs up first customer for Internet–based healthcare service, InfoWorld Electric, pp. 1–2, Jun. 26, 1996.

*Primary Examiner*—John P. Lacyk
*Assistant Examiner*—Michael Astorino
*Attorney, Agent, or Firm*—Dorsey & Whitney, LLP

[57] ABSTRACT

A medical diagnostic enhancement method and system for determining diagnostic tasks to fine-tune a patient diagnosis based upon a possible diagnosis and acquired data for the patient. With this method, a presenting problem is received. Responsive to the presenting problem, particular patient data is then collected. Next, based on predetermined criteria, a plurality of possible diagnoses are presented for selection by a user. The user is then provided with a recommended diagnostic task based on the selected possible diagnosis. The system is a repository of the results of the diagnostic task or it can continue to process the patient data for other suspected diagnoses.

21 Claims, 24 Drawing Sheets

Joint Pain Suspected Diagnoses/Signs and Symptoms

Ankylosing spondylitis

| Subjective | Objective | Other Information |
| --- | --- | --- |
| - May have pain in peripheral joints<br>- Back pain<br>- Early Morning stiffness<br>- Fatigue<br>Signs of IBD<br>- Anorexia<br>- Diarrhea<br>- Weight loss<br>- Anemia<br>- Fever | - Kyphosis - late stages<br>- Elevated IgA levels<br>- HLA-B27 antigen positive<br>- Mildly elevated sed. rate | - Hx inflammatory bowel disease<br>- Male Predominance |

Avascular necrosis

| Subjective | Objective | Other Information |
| --- | --- | --- |
| - May hae referred knee pain<br>- Pain with weight bearing | - Internal rotation of the hip is painful | - Associated with trauma, SLE, gout, sickle cell disease, alcoholism, pancreatitis<br>- Coomplication of corticosteroid use<br>- Most often affects hip or knee, other possible sites are ankle, shoulder, and elbow |

Bone Tumors - Benign

| Subjective | Objective | Other Information |
| --- | --- | --- |
| - Localized pain<br>- Pain may be more severe at night<br>- Pain may be relieved by Aspirin<br>- Pain may be aggravated by weight bearing | - Swelling<br>- May have palpable mass<br>- Tenderness | - May have incidental findings on radiographic exams |

Bone Tumors - Primary Malignant

| Subjective | Objective | Other Information |
| --- | --- | --- |
| - Pain often occurs at night<br>- Pain often occurs at rest<br>- Pain may be aggravated by wt. bearing<br>- Weakness<br>- Fatigue | - Wt loss<br>- Swelling<br>- Asymmetry between joints<br>- Tenderness<br>- Temperature changes on palpation | - Pain usually increases as disease spreads |

*Fig. 3A*

Joint Pain Patient Questionnaire

1. Which joints are painful to you. (Check all that apply)

____ Shoulder      ____ Right ____ Left ____Both
    ____ Elbow         ____ Right ____ Left ____Both
    ____ Wrist         ____ Right ____ Left ____Both
    ____ Hip           ____ Right ____ Left ____Both
    ____ Knee          ____ Right ____ Left ____Both
    ____ Ankle         ____ Right ____ Left ____Both
    ____ Fingers       ____ Right ____ Left ____Both
    ____ Elbow         ____ Right ____ Left ____Both
    ____ Foot          ____ Right ____ Left ____Both 2. Did you have an injury?    ____ No    ____ Yes, When? _____
   Occurred at Work? ____ No    ____ Yes 3. Did the pain start suddenly?    ____ No    ____ Yes 4. How long has this episode of pain lasted? _____

5. Have you had previous episodes of joint pain?____ Yes    ____ No

6. How Long has previous episodes of pain lasted? _____

7. How does the pain feel to you? (Check all that apply)

____ Constant         ____ Dull              ____ Sharp
    ____ Intermittent     ____ Burning           ____ Tingling
    ____ Shooting         ____ Worse in the morning
    ____ Worse at night   ____ Pain without movement
    ____ Pain with weight bearing 8. How would you rate your pain?

1         2         3              4         5
   Mild                Moderate                 Severe 9. Does the pain limit your normal daily activities? ____ No    ____ Yes 10. What activities are hard for you to do now that you could easily do before the start of the pain? _____

11. Is there anything you do that makes the pain less?
    _____

12. What causes the pain to get worse?
    _____

13. What is your occupation? _____

14. Is your work activity limited?    ____ Yes    ____ No

*Fig. 3B*

Joint Pain Imaging Choices

| Suspected Diagnosis | Initial Imaging | Alternative Imaging |
|---|---|---|
| Ankylosing Spondylitis | Plain films of pelvis | CT for detection sacroiliac changes |
| Avascular Necrosis | Plain Films - if plain films negative and still suspect, need to do an MRI or CT | MRI sensitive to early diagnosis |
| Bone Tumors - Primary (Maglinant or Benign) | Plain Films | MRI or CT |
| Bone Tumors - Metastastic | Nuc Med Bone scan | MRI or CT for detail of extent of disease (Spine-MRI) |
| Bursitis | Shoulder and hip bursitis should have Plain films done | MRI - later stages for possible tendon abnormalities |
| Calcific Tendonitis | Plain films | CT |
| Charcot Joints (Neuropathic joint disease) | Plain Films | MRI may be needed to R/O osteomyelitis |
| Chondromalacia Patella | Not Indicated | Consider Plain films if poor response to therapy MRI |
| Degenerative Joint Disease | Plain films | Nuc. Med - Hip joint MRI - to evaluate cartilag CT |
| Dislocation | Plain films | CT - trauma<br>MRI - if pain persists, to detect soft tissue damage |
| Fracture | Plain films | CT - fractures<br>MRI - soft tissue damage<br>Nuc Med - Stress fractures |
| Gout | Not Indicated - early stages | Plain films - late stages |
| Pseudogout | Not Indicated - early stages | Plain films - late stages |

*Fig. 5*

RECOMMENDATION

| Procedure Category | Magnetic Resonance Imaging |
|---|---|
| Procedure Code | 70553 |
| Procedure Modifier | 00 |
| Description | Magnetic Image - Brain |
| Radwise Text | Contrast May be indicated. CT if unable to have an MRI |

478

- Accept this recommendation and create service record
- Create Different Service Record
- Guideline Abstract
- Reference List
- Cancel

476

Case Summary Report
Headache
Nelson, Tracy P
Encounter?

Encounter
10/21/1998
Harowski, Connie J.
Questionnaire
Completed - 10/21/1998
Guideline
Completed - 10/21/1998
Suspected Diagnosis
Neoplasm of Unspecified Nature of Brain
Services?

*Fig. 22*

SERVICE TYPE

Select A Service Type

- Behavior Modification
- Follow-Up Visit
- Home Care Evaluation
- Occupational Therapy
- Other
- Over-the-Couner Med
- Physical Therapy
- Prescription Med
- Radiology
- Specialist Evaluation Next Cancel

Radwise System - Intelligent Radiology Management - Microsoft Internet Explorer

RADWISE

Case Summary Report
Headache
Nelson, Tracy P
Encounter?

Encounter
10/21/1998
Harowski, Connie J.
Questionnaire
Completed - 10/21/1998
Guideline
Completed - 10/21/1998
Suspected Diagnosis
Neoplasm of Unspecified Nature of Brain
Services?

Service Provider

| | | Name | City | Phone |
|---|---|---|---|---|
| ○ | 1 | Central City Radiology | Minneapolis | 612-555-4369 |
| ○ | 2 | Imaging Center | St. Louis Park | 612-555-8756 |
| ○ | 3 | Radical Radiologists | Waite Park | 320-251-0067 |

[Previous]  [Next]

Different Services Selected — Internet Zone

Radwise System - Intelligent Radiology Management - Microsoft Internet Explorer

RADWISE

Case Summary Report
Headache
Nelson, Tracy P
Encounter?

Encounter
10/21/1998
Harowski, Connie J.
Questionnaire
Completed - 10/21/1998
Guideline
Completed - 10/21/1998
Suspected Diagnosis
Neoplasm of Unspecified Nature of Brain
Services?

Service Confirmation

| Status | Service Recommendation Accepted |
|---|---|
| Provider | Radical Radiologists |
| Procedures | Magnetic Image - Brain |
| | |

[Previous]  [Cancel]
[Save And Order Another Service]  [Save and Exit]

javascript.xdo.Submit(saveexit). — Internet Zone

Fig. 28

Radwise System - Intelligent Radiology Management - Microsoft Internet Explorer

RadWise

Case Summary Report
Headache
Nelson, Tracy P
Encounter?

Encounter
10/22/1998
Tesla, MD, Randy M.
Services Pending
MRI-10/22/1998

Encounter
10/22/1998
Harowski, Connie J.
Questionnaire
Completed - 10/22/1998
Guideline
Completed - 10/22/1998
Suspected Diagnosis
Neoplasm of Encounter Date: 10/22/1998
Provider: Radical Radiologists
Encounter Type: Special Visit   ☐ Create Patient Login — 484

|   |   | Last Name | First Name | Provider # | Speciality |
|---|---|---|---|---|---|
| ○ | 1 | Roentgen, MD | Ray | 41-9999999 | Radiology |
| ◉ | 2 | Tesla, MD | Randy | 41-9999999 | Radiology |

Cancel    Undo    Save this encounter data

Radwise System - Intelligent Radiology Management - Microsoft Internet Explorer

RadWise

Work Queue
Referrals
Cases in Process
Clinical Findings
Case Errors
Case Archives
486 — Initiate Case
Member Inquiry
Provider Inquiry
Practitioner Inquiry
Exit RadWise System

Work Queue - Cases in Proces
Cases Found: 6                                    Search

| | Practitioner | Patient Name | Date of Birth | Presenting Problem | Encounter Date |
|---|---|---|---|---|---|
| 1 | Roentgen, MD, Ray R. | Harris, Paul M. | 09/10/1963 | Low Back Pain | 09/17/1998 |
| 2 | Roentgen, MD, Ray R. | Johnson, Fern H. | 05/25/2010 | Headache | 09/15/1998 |
| 3 | Roentgen, MD, Ray R. | Nelson, Scott J. | 05/09/1956 | Abdominal Pain - Male | 09/22/1998 |
| 4 | Tesla, MD, Randy M. | Austin, Nicole M. | 03/28/1974 | Abdominal Pain - Female | 09/07/1998 |
| 5 | Tesla, MD, Randy M. | Johnson, Fern H. | 05/25/2010 | Headache | 09/13/1998 |
| 6 | Tesla, MD, Randy M. | Nelson, Tracy P. | 01/16/1960 | Headache | 10/22/1998 |

485    Clear Search

DIAGNOSTIC ENHANCEMENT METHOD AND APPARATUS

1. TECHNICAL FIELD

The present invention relates generally to a diagnostic enhancement method and system. In particular, the present invention relates to a system for managing and improving patient diagnoses.

2. BACKGROUND OF THE INVENTION

In diagnosing a pathology, a doctor exercises his/her medical experience and knowledge to identify a suspected diagnosis based on a set of reported and/or observed patient symptoms. Unfortunately, the effectiveness of this methodology depends on the subjective ability of the individual doctor to collect data on patient signs and symptoms and select among the possible diagnoses. Additionally, even the most qualified doctors, for whatever reason, may not consider lesser known or seemingly unlikely diagnoses. On the other hand, machines such as medical expert systems can not replace a creative, open-minded, insightful physician. Complete (or even substantial) reliance on a machine for diagnosing a patient in many cases would be deemed unwise. Thus, a solution is needed for assisting a doctor, regardless of his/her expertise or training, in diagnosing a patient pathology.

In addition, various medical professionals including nurses, doctors, physician assistants, laboratory technicians, and specialists such as radiologists can be involved with the diagnosis of a patient. Normally, general patient data is initially obtained by a nurse and then provided to the patient's primary care physician ("PCP") who proceeds to examine and diagnose the patient. In some cases, the PCP will require that a diagnostic task such as a laboratory test or a medical imaging procedure be performed in order to help pinpoint or confirm a suspected diagnosis. The PCP will usually take steps to initiate execution of this task, but he/she may not provide the task performer with suitable patient data or precise enough instructions to ensure that the task is performed both efficiently and effectively in connection with the suspected diagnosis. In some cases, the task performer (e.g., radiologist) needs to contact the PCP in order to acquire necessary patient information. Unfortunately, this takes time away from both the task performer as well as that of the PCP. In other cases, the PCP requests a diagnostic task that is inappropriate or not needed which unnecessarily adds to the cost of healthcare; some tests, such as a magnetic resonance image ("MRI") may be extremely costly.

Accordingly, what is needed is a method for assisting a physician in accurately and efficiently diagnosing a patient. Moreover, what is needed is a system for managing and improving the diagnostic process including the recommendation and performance of diagnostic tasks.

3. SUMMARY

The present invention provides a diagnostic enhancement method and system. In one embodiment, a diagnostic enhancement program is provided that when executed performs a diagnostic enhancement method. With this method, a presenting problem is received by the system. Responsive to the presenting problem, particular patient data is then collected. Next, based on criteria applied to the patient data, a plurality of possible diagnoses is presented for selection by a user. After the user selects a diagnosis, the system provides a recommended diagnostic task based on the selected possible diagnosis.

4. BRIEF DESCRIPTION OF THE DRAWINGS

FIG. 3A depicts a portion of an exemplary diagnostic guideline, with joint pain as the presenting problem.

FIG. 3B depicts a portion of an exemplary questionnaire, with joint pain as the presenting problem.

FIG. 5 shows a portion of a table of recommended imaging choices for some diagnoses relating to joint pain as the presenting problem.

FIGS. 6 through 36 show screen printouts from an exemplary case diagnosis using one embodiment of a diagnostic enhancement system with a "headache" as the presenting problem.

5. DETAILED DESCRIPTION

A diagnostic enhancement system is provided for assisting users (e.g., primary care physicians, specialists, physician assistants, nurses) in diagnosing patient pathologies. In addition, the system may be used to manage and monitor both the efficiency and efficacy of medical diagnoses. Unnecessary or inappropriate diagnostic tasks, such as certain medical imaging procedures, may be reduced with the diagnostic enhancement system, because it promotes an efficient, systematic approach to pathology diagnosis and appropriate selection of diagnostic testing. In one embodiment of the present invention, a diagnostic enhancement system is implemented with a diagnostic enhancement server application that is made available to a plurality of user (e.g., subscriber) clients.

5.1 System Overview

Figure 1:
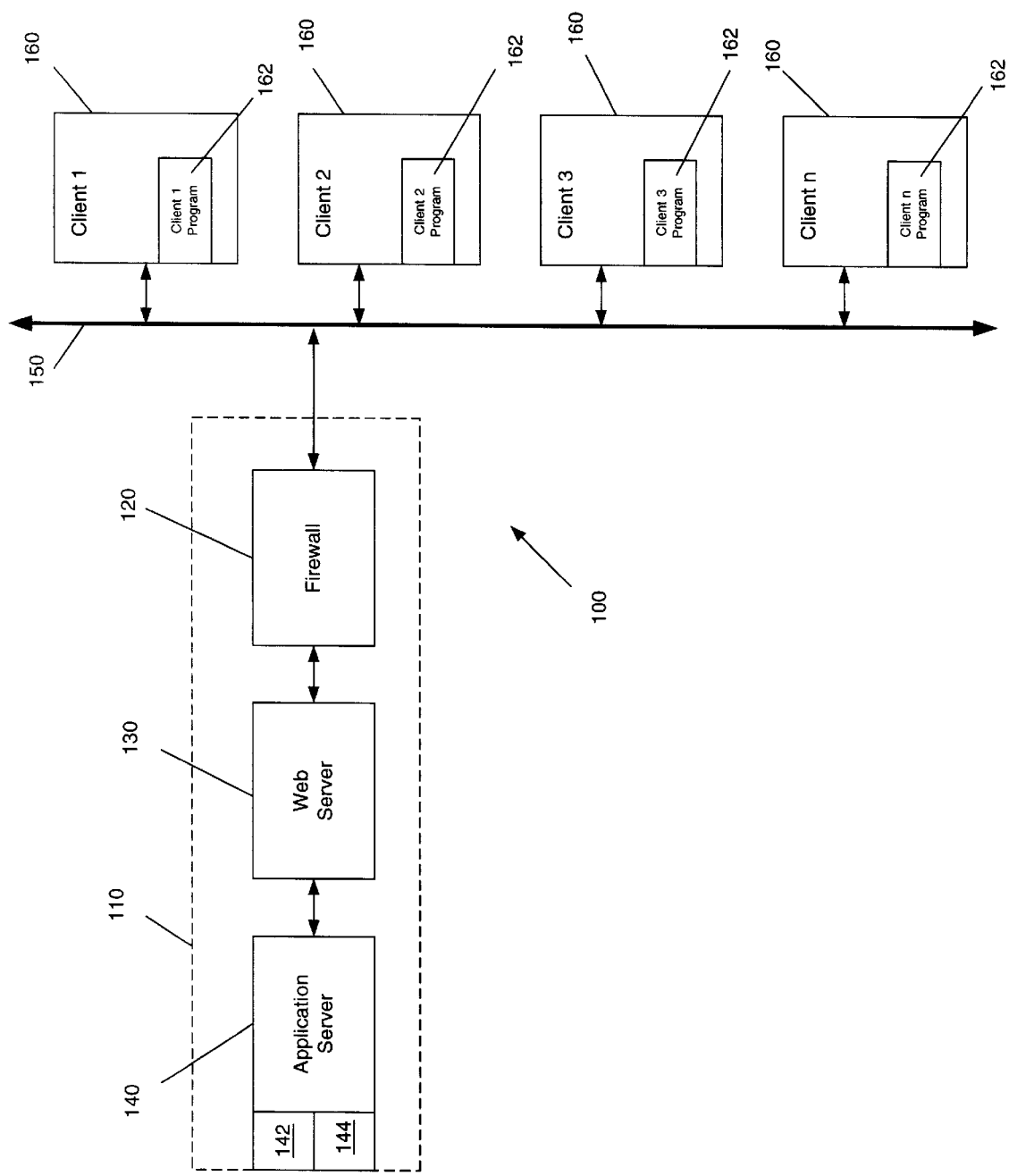
FIG. 1 shows a block diagram of one embodiment of a diagnostic enhancement system.

FIG. 1 shows one embodiment of a diagnostic enhancement system of the present invention. In this embodiment, the diagnostic enhancement system 100 is implemented using the Internet. System 100 comprises a server system 110 in Internet network communication with a plurality of clients 160 via network communication interface 150. The server system 110 includes a firewall 120 interposed between the network communications interface 150 and a web server 130 linked to an application server 140. The web server 130 is in communication with the application server 140. The application server 140 includes diagnostic enhancement program 142 and database/database program 144. Each of the clients 160 includes a client program 162 (e.g., any suitable Internet browser) to enable a user to communicate with the diagnostic enhancement program 142.

Firewall 120 may be any suitable device (or software in a router) that links the server system 110 (e.g., an organization's internal TCP/IP network) to the Internet and restricts the types of traffic that it will pass, to provide security. In addition, firewall 120 can require users (as subscribers) to log in to the server system 110 in order to obtain access to the diagnostic enhancement program 142.

Web server 130 is a conventional web server. It allows the diagnostic enhancement program 142 to be accessed over the Internet. Web server 130 accepts incoming requests from clients 160 and then returns appropriate documents (e.g., HTML, J-Script documents). Web server 130 may be implemented with any suitable computer executing an appropriate web server program, e.g., Microsoft's MSIIS™.

The diagnostic enhancement application server 140 may also be implemented with any suitable computer for executing diagnostic enhancement program 142 and the database/database program 144. The purpose of the diagnostic enhancement program 142, in connection with the database/database program 144, is to perform a diagnostic enhancement routine (which will be discussed in greater detail below) in order to assist and monitor users in diagnosing patient pathologies and selecting, ordering and reporting on appropriate diagnostic tests. The diagnostic enhancement program 142 may be implemented with any suitable server side (or even client side, e.g., JavaScript) application scheme using an adequate programming structure and language. For example, the diagnostic enhancement program 142 could be implemented with a common gateway interface ("CGI") script application, or more particularly with Microsoft's ISAPI™ or Netscape's NSAPI™ application development software. Likewise, any suitable database program may be used to implement the database/database program 144. For example, in one embodiment, the database/database program 144 is implemented with Webspeed 4GL™ and Progress Enterprise Database™, available from Progress Software Corp. of Bedford, Mass.

Skilled artisans will recognize that the diagnostic enhancement program 142 and the database/database program 144 may be operably implemented on different server computers. In addition, the diagnostic enhancement system 100 may be implemented in any suitable client/server network environment such as a local area network ("LAN"), a wide area network ("WAN"), or an alternate type of internetwork. Moreover, any one of a variety of client/server architectures may be used, including but not limited to TCP/IP (HTTP network), NAS and SAA. Furthermore, although the diagnostic enhancement system 100 of FIG. 1 depicts only one server system 110, it should be recognized that more than one server system 110 could be used, depending upon particular network requirements. For example, multiple redundant servers could be implemented for both faster operation and enhanced reliability. Also, additional servers could be used for various alternative functions (e.g., as a gateway) within server system 110.

5.2 Diagnostic Enhancement Routine

Figure 2:
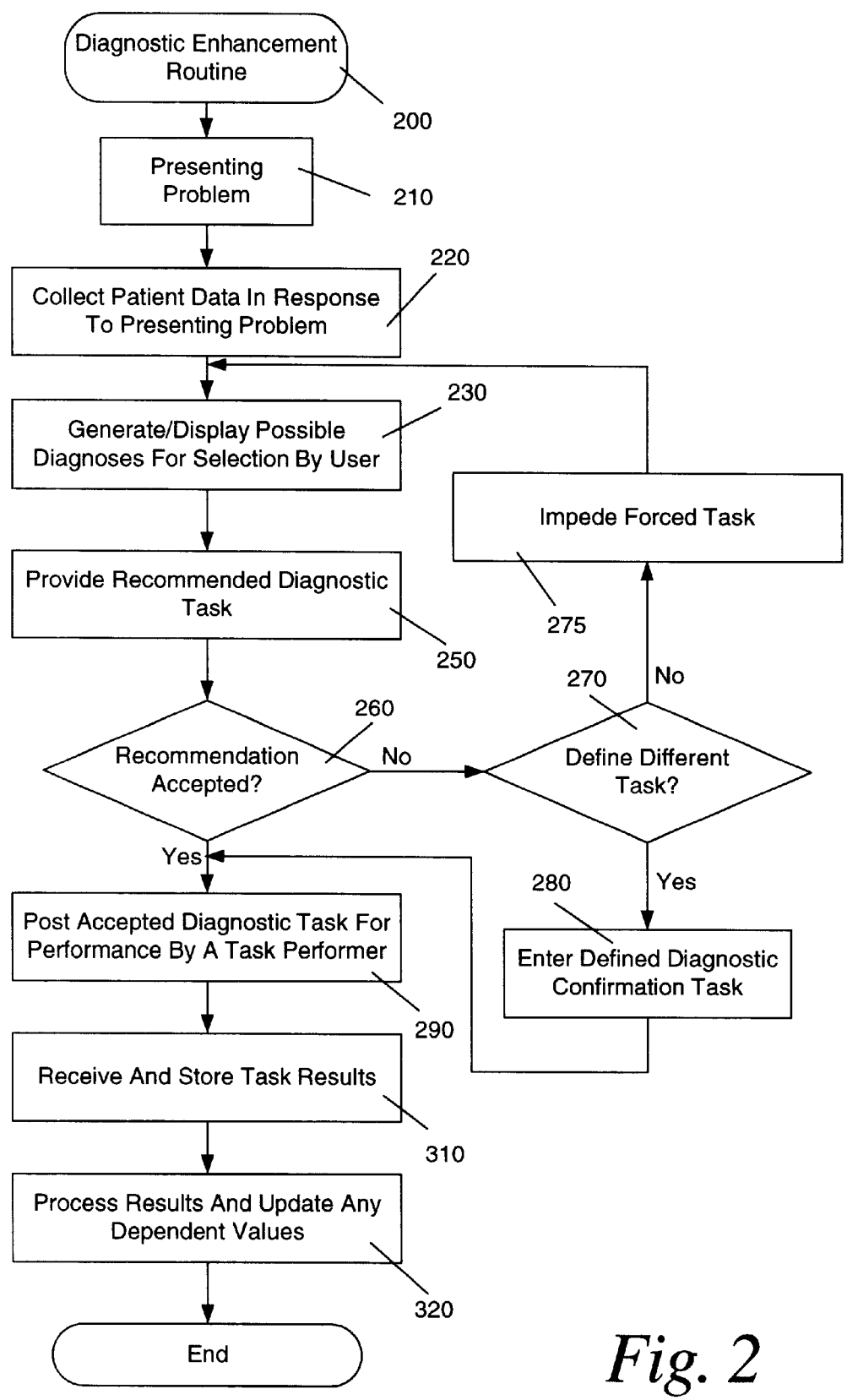
FIG. 2 shows a flowchart of one embodiment of a diagnostic enhancement routine.

FIG. 2 shows an overview of one embodiment of a diagnostic enhancement routine 200, which is performed by the executing diagnostic enhancement program 142. Further details of the steps involved (including terms used) are presented in sections 5.2.1 to 5.2.5 below. Initially, at 210, a patient's presenting problem is entered into (and received by) the system, i.e., the executing diagnostic enhancement program 142. Next at 220, in response to the particular presenting problem, the system guides collection of additional patient data (e.g., symptoms) which are entered into the system. At 230, based on evaluation of the presenting problem and/or the collected patient data, the system presents a list of possible (or probable) diagnoses to the user for his/her selection of a first diagnosis. After the user has selected a possible diagnosis, in response to the selected diagnosis, the system provides the user with a recommended diagnostic task at 250. At this point, the user may either accept or reject the recommended diagnostic task at 260. If the user declines the recommended task, he/she is then given the option to self-define and/or enter into the system a different task (along with an explanation, in some cases) at 270. If the user decides not to enter a self-defined task at 270, the user returns to step 230 by way of step 275. The purpose of step 275 is to collect information on the user's reasons for not proceeding to select a diagnostic task presented by the system or a self-defined task and to provide a deterrent to a user simply repeatedly returning to the list of possible diagnoses to make a new, unreasoned selection, in the hope that the selection will lead to the user's preferred diagnostic task. This impedes a "forced" task contrived by the user. At 230 the list of possible diagnoses is once again displayed for selection of an alternative diagnosis by the user. Alternatively, if the user has chosen to self-define her/his own diagnostic task at 270, the self-defined task is entered into the program at 280. Thus, at 290, either a recommended diagnostic task (if accepted by the user at 260) or a self-defined diagnostic task (from 280) is "posted" into the system. At 310, after the posted task has been communicated to and performed, either by a user or other specially qualified person such as a radiologist, the system receives and stores the results of the diagnostic task and enters them into the database/database program 144. Finally, at 320, the program processes the results and updates any dependent values. Based on the diagnostic task results, a system user can make a second diagnosis, which may be the same as the first diagnosis (confirmation) or be different.

5.2.1 Presenting Problem

A "presenting problem", which is received by the system at 210, may be the general (and usually predominant) condition or symptom of the patient. While it typically will be described by the patient, it may also be observed by a health care provider or result from a simple, initial diagnostic procedure. Based on the particular presenting problem, additional data (or symptoms) are collected from the patient in order to help pinpoint a diagnosis. In one embodiment of the invention, five specific presenting problems, including headache, joint pain, low back pain, neck pain, and abdominal pain (male or female), are used by the system to lead to guideline-based data collection procedures specifically oriented to the particular presenting problem. However, in other embodiments, any number of presenting problems could be utilized depending on the parameters and objectives of the particular system.

5.2.2 Patient Data Collection

At 220, patient data, including symptoms, are collected based (at least in part) on the particular presenting problem received by the system. Each guideline-based data collection procedure may be a separate questionnaire or script. Alternatively, the guideline-based data collection procedure can be a set of procedures with multiple paths that are interactively selected based not only on a particular presenting problem but on other data points collected as the user works through the guidelines. In many cases, the most important aspect of evaluating a patient, prior to the diagnostic task (which may be a test to acquire additional information or to confirm a suspected diagnosis), is a thorough history and physical examination of the patient. In fact, one study has shown that the patient history can provide up to 80% of the needed information, with the physical exam providing 15%, and the diagnostic tasks only providing 5%. Therefore, it is important to acquire as much patient data from the patient's history and physical examination as is reasonably possible before performing diagnostic tasks, which can be costly and in some cases, even detrimental to the patient's health.

In one embodiment, in order to acquire relevant patient data that will lead to an accurate diagnosis, diagnostic clinical guidelines are formulated to correlate a group of potential diagnoses with each presenting problem. In turn, relevant patient data/symptoms are associated with each of the potential diagnoses. These guidelines are built to provide both a guide to effective data collection on the patient and to develop predetermined criteria that help connect patient data/symptom sets with one or more likely diagnoses.

Evidence-based methods, along with expert panel review, are used to develop the clinical guidelines. This methodology also meets the standards for guideline development as defined by the American Association of Health Plans (AAHP). The relevant literature is rigorously analyzed, and key patient symptoms are identified. This information may then be synthesized into multiple guideline pathways with the supporting evidence being documented. Once formulated, the guidelines are then subjected to expert panel review. The expert panels may be composed of various members (e.g., nurses, primary care physicians, and specialists including radiologists) from the medical community. The guidelines may then be revised in accordance with this review by the expert panel. At this point, the guidelines are then incorporated into the diagnostic enhancement system as: (a) guides for patient data collection; and (b) logical engines for linking symptoms/patient data to diagnoses. However, it is important to note that these guidelines are dynamic in that they are always subject to improvement through revision in response to new findings in medical literature and analysis of data gathered by the system. FIG. 3A illustrates a portion of an exemplary diagnostic guideline for "joint pain" as the presenting problem.

Among other things, the guidelines are used to determine which patient data should be elicited in response to the particular presenting problem. This targeted data, which is collected in routine 200 at 220, is acquired in two steps. Initially, the system provides a user with a questionnaire that is designed to elicit patient data from a user (e.g., patient, receptionist) who is not necessarily as qualified clinically as a trained medical professional. FIG. 3B shows an example of a portion of a patient questionnaire—again, with the presenting problem being joint pain. After the questionnaire has been completed and entered, the system next guides and solicits data from a medical professional who performs a patient examination. The patient data resulting from both the questionnaire and the patient examination are entered into and collected in the system.

5.2.3 Display of Possible Diagnoses

Figure 4:
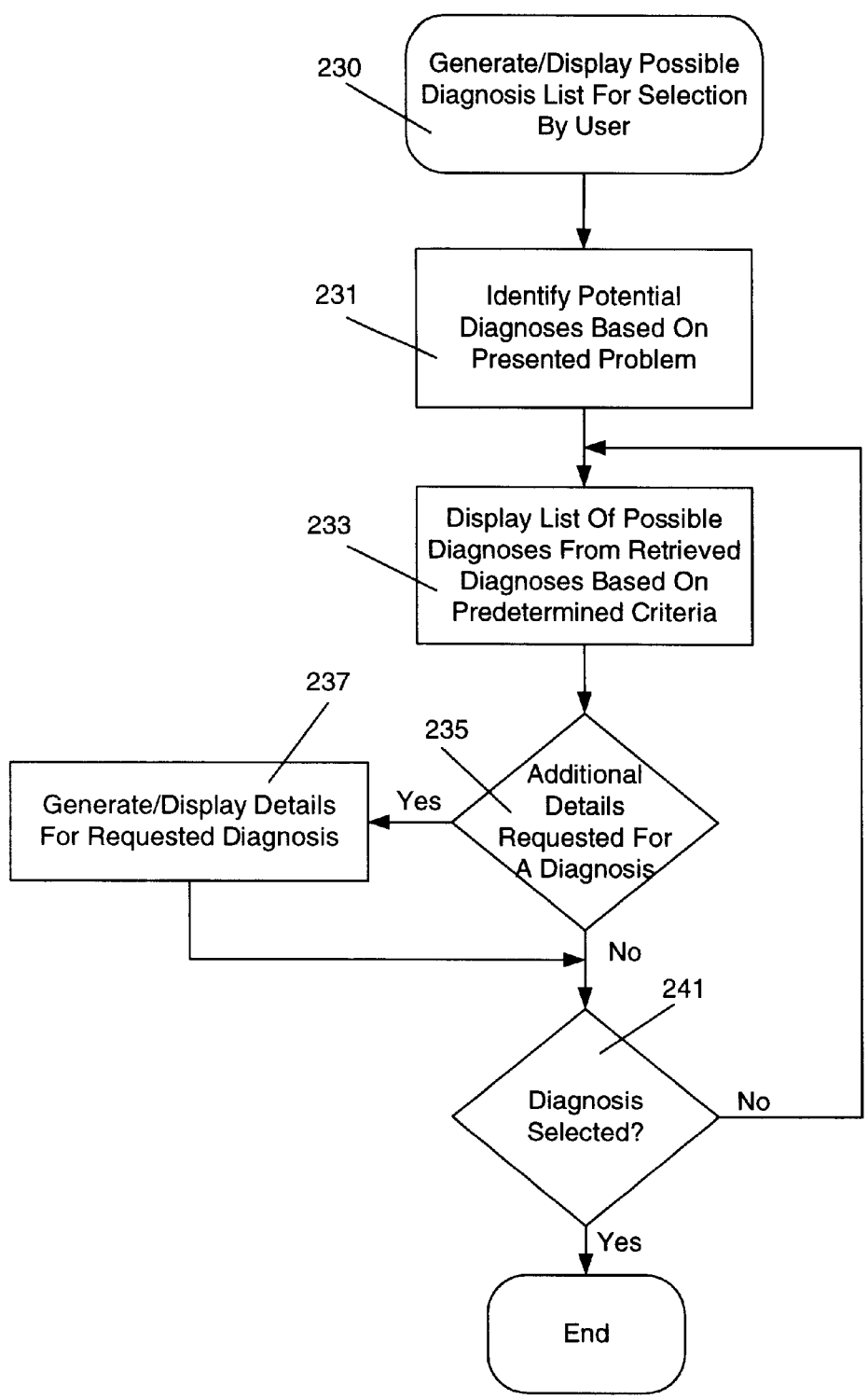
FIG. 4 shows a flowchart of a routine for generating and displaying possible diagnoses for selection by a user.

FIG. 4 shows one embodiment of a routine 230 for generating and displaying possible diagnoses for selection by a user. Initially, at 231, the routine identifies a broad set of potential diagnoses based on the presenting problem. Next, at 233, a list of possible diagnoses is retrieved from the broad set of potential diagnoses based on predetermined criteria linking observed patient data and particular diagnoses. This list is then presented to the user for selection of a diagnosis. At 235, the routine assesses whether additional details have been requested by the system to further aid diagnosis. If additional details have been requested, the routine generates and displays the additional information requested to aid diagnosis and receives any new data supplied by the user at 237. Next, at 241, regardless of whether additional details were requested or not, the routine determines whether a diagnosis has been selected by the user. If so, routine 230 is completed and returns control to routine 200 to proceed to step 250. On the other hand, if a diagnosis has not been selected at 241, routine 230 allows a user to return to 233 to display the list of possible diagnoses until a diagnosis is selected.

The set of potential diagnoses, which is identified at step 231, may be identified (or obtained) from the previously discussed diagnostic guidelines. This set of diagnoses can include hundreds or even thousands of potential diagnoses. For example, in one embodiment, over 300 potential diagnoses were identified with a "headache" as the presenting problem. In addition, in the one embodiment, the physician may add an additional diagnosis to the list of potential diagnoses.

The list of possible diagnoses, which is obtained from the broad set of potential diagnoses based on predetermined, guideline-based criteria, are presented to the user at 233. The particular predetermined criteria are applied to the presenting problem, the collected patient data, or a combination of both the presenting problem and collected patient data. Each diagnosis has a set of associated symptoms that are derived from a diagnostic guideline. A "symptom hit" for a particular diagnosis occurs when the patient exhibits a symptom from the set of symptoms associated with the particular diagnosis. In one predetermined criteria scheme, all diagnoses (from the set of potential diagnoses) that have at least one symptom hit are presented to the user in the list of possible diagnoses. With a more advanced set of criteria that sharply limit the list, the list might be better viewed as a list of "probable" diagnoses. However, any suitable predetermined criteria scheme could be used to select a set of diagnoses that will help guide the user's judgement.

In 235 and 237, the user is given the option to receive additional details for a selected diagnosis from the list of possible diagnoses. In general, these details help explore the likelihood that the patient has the selected possible diagnosis. For example, the additional details could be as simple as a presentation of the requested diagnosis' full set of associated symptoms with identification of the symptom hits. Alternatively, elaborate statistical data for the associated symptoms' relationship to the diagnosis could be presented. Such data could include individual symptom correlation statistics or weighting. For example, with joint pain being the presenting problem, a benign bone tumor (as shown in FIG. 3A) may have seven identified, associated symptoms including localized pain, pain more severe at night, pain reduced by aspirin, pain aggravated by bearing weight, swelling, palpable mass, and tenderness. Over time, the system may determine that having a palpable mass is more determinative for the benign bone tumor diagnosis than having any of the other symptoms. Thus, correlation levels or weighted values could be determined for each symptom and presented to the user. For example, on a scale from 1 to 5, a palpable mass could have a value of 4, in a benign bone tumor diagnosis whereas any of the first four symptoms might only have a value of 1.

5.2.4 Diagnostic Task

With reference once again to FIG. 2, at 250 through 290 an accepted diagnostic task is processed by the system for communication to and performance by a task performer. Initially, at 250, a recommended task, responsive to the selected possible diagnosis, is presented to the user. A diagnostic task may be any task or procedure for acquiring additional data related to the possible diagnosis or for confirming the possible diagnosis. Such tasks include but are not limited to laboratory tests and medical imaging procedures such as x-ray technology, computed radiography, magnetic resonance imaging ("MRI"), computed tomography ("CT"), ultrasound imaging, nuclear medicine, and mammography imaging. By use of carefully-developed guidelines, the system can be programmed to select an appropriate diagnostic task for recommendation. Appropriateness means both that the diagnostic test is medically appropriate for the selected diagnosis and the particular patient, but also that the diagnostic task is cost-effectively matched to the selected possible diagnosis. For example, FIG. 5 shows a portion of a table of recommended imaging choices for some selected diagnoses (or selected possible diagnoses) relating to joint pain. As shown in FIG. 5, the recommended task may include a logically ordered list of several tasks to be successively performed until a diagnosis can be confirmed. In this manner, costly procedures may be deferred and ultimately avoided.

At 260, the user is given the opt ion to either accept or reject the recommended task. If the user decides not to accept the recommended task, he/she can define a different, self-defined task at 270. This feature provides the user with flexibility in diagnosing the pathology. It should be remembered that the diagnostic enhancement system 100 is a diagnostic aid for assisting (not replacing) the skilled medical professional. If the user decides to use a self-defined task, this task is entered into the system at 280. Otherwise, routine 200 returns to 230 (by way of step 275) to enable the user to select a different possible diagnosis. As explained above, in the depicted embodiment, the step at 275 is designed to deter system misuse. This inhibits a user from "cheating" the system by selecting different possible diagnoses until a desired diagnostic task is recommended by the system.

At 290, the system posts an accepted diagnostic task, which may be a recommended task from 260 or a self-defined task from 280. Posting each accepted task is necessary in order to initiate its performance and later process its results. One aspect of the present invention is that user clients 160 may be geographically located anywhere in the world so long as they have access to system 100 through a client 160. In this manner, when a patient is diagnosed using system 100 by a first user or users in a first location (e.g., a local clinic), a second user (e.g., radiologist) in a wholly different location can perform the posted diagnostic task, as specified by the first user, with all of the patient's relevant data conveniently at the disposal of the second user. Furthermore, the first user doesn't have to communicate directly with the second user in order to initiate the performance of the task; rather, the first user must simply "post" the task into the system. The second user can then retrieve the posted task at a convenient time, with or without receiving a prompting notice. Moreover, additional information such as abstract explanations and source references may be readily provided to the second user (e.g., through hypertext links) to support the system's recommended diagnostic task. This additional material can all be studied at a time selected by the second user.

5.2.5 Receive and Process Task Results

In routine 200 at 310 and 320, the results of the task are received, stored and processed by the system. These results could be test data results, or they could be diagnostic to conclusions or finding codes, as determined by the user who performed the diagnostic task. For example, if the purpose of the task was to confirm a selected (or suspected) diagnosis, the task performer, e.g., radiologist, could report to the system whether or not the suspected diagnosis was confirmed and if not, whether a different pathology was detected. This type of information is useful in assessing the performance of the system, as well as the performance of the users. In addition, other information may be provided from the task performer such as particular information for assisting the first user in treating the patient. Again, this posted information can be retrieved and reviewed at a time selected by the next user.

At 320, the results are stored in database 144, and any dependent values are updated. These dependent values could include performance parameters for evaluating system users, statistical or weighting values used in selecting diagnoses, and any other values used in the various processes of routine 200. In this manner, the system is capable of monitoring and evaluating the performance and efficiency of the diagnostic process. In addition, the guidelines and recommended tasks may be revised in response to these results in order to improve the operation of the overall system.

5.3 EXAMPLE

Figure 6:
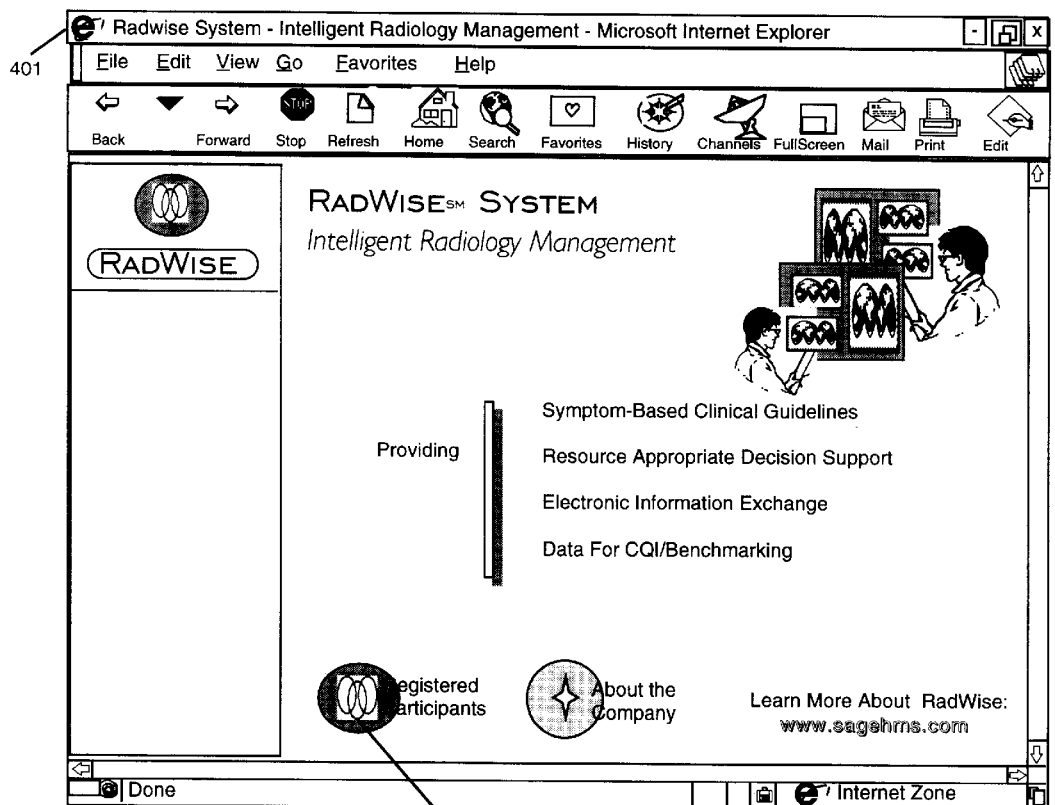

FIGS. 6 through 33 show screen printouts from an exemplary case diagnosis using one embodiment of a diagnostic enhancement system with a "headache" as the presenting problem. These screen printouts were taken from a client 160. FIG. 6 shows a splash page, which provides the user with entry into the diagnostic enhancement system 100. Note that in the depicted embodiment, the address of this splash (or home) page at 401 indicates that the system is actually being implemented on an internal HTTP network called "Radwise Login." However, the relevant aspects of how the system functions would be the same when implemented on the Internet. In addition, it can be seen that in this example, Microsoft's Internet Explorer™ browser is used as the client program 162 for the system 100. In order for the user to invoke the system 100, it selects the hypertext link at 403, which is labeled Registered Participants.

Figure 7:
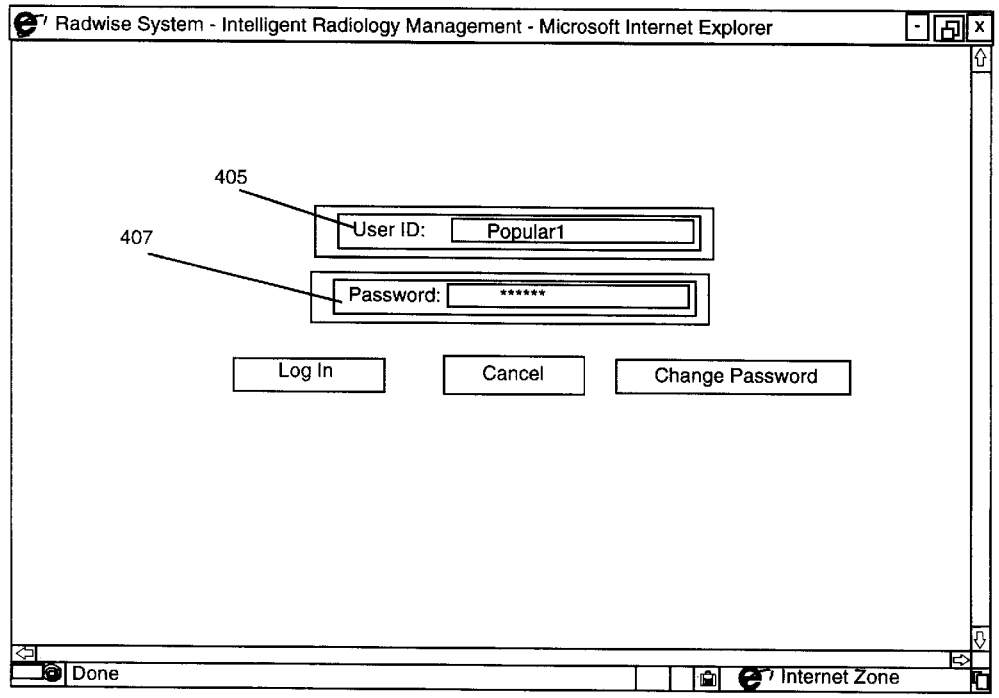
Figure 8:
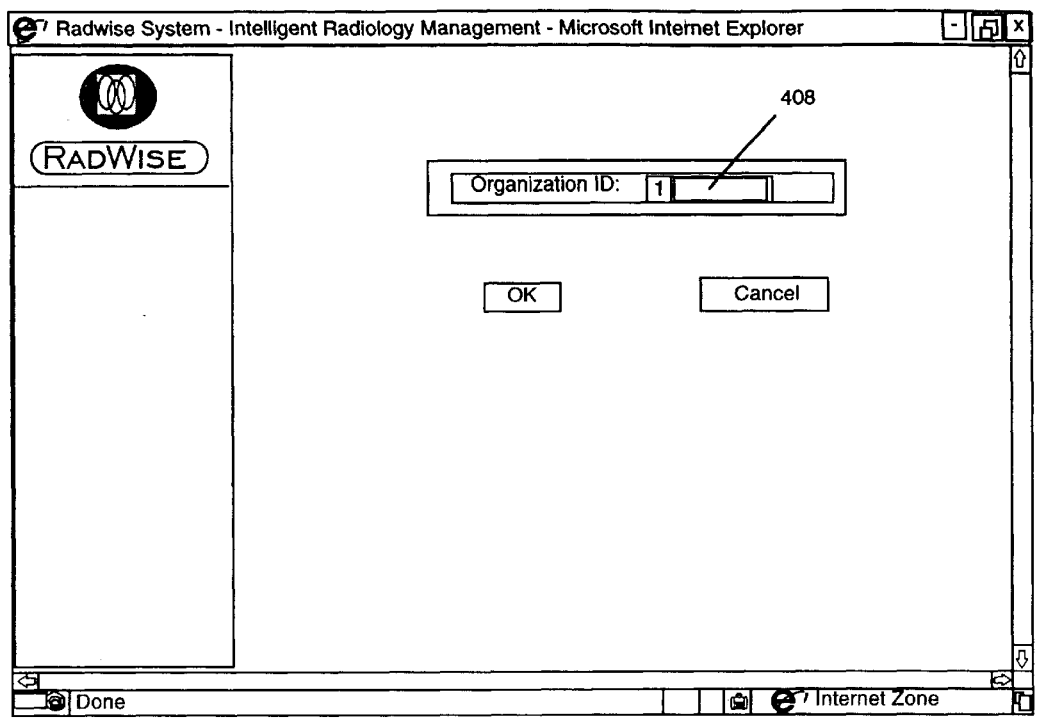

FIG. 7 shows the next page, which is the security screen. With this page, each user must log into the system with a User ID at 405 and a Password at 407. As shown in FIG. 8, an individual organization (e.g., clinic, HMO) can have its own unique set of usernames (or identification strings), which may be entered into the Organization ID field 408.

Figure 9:
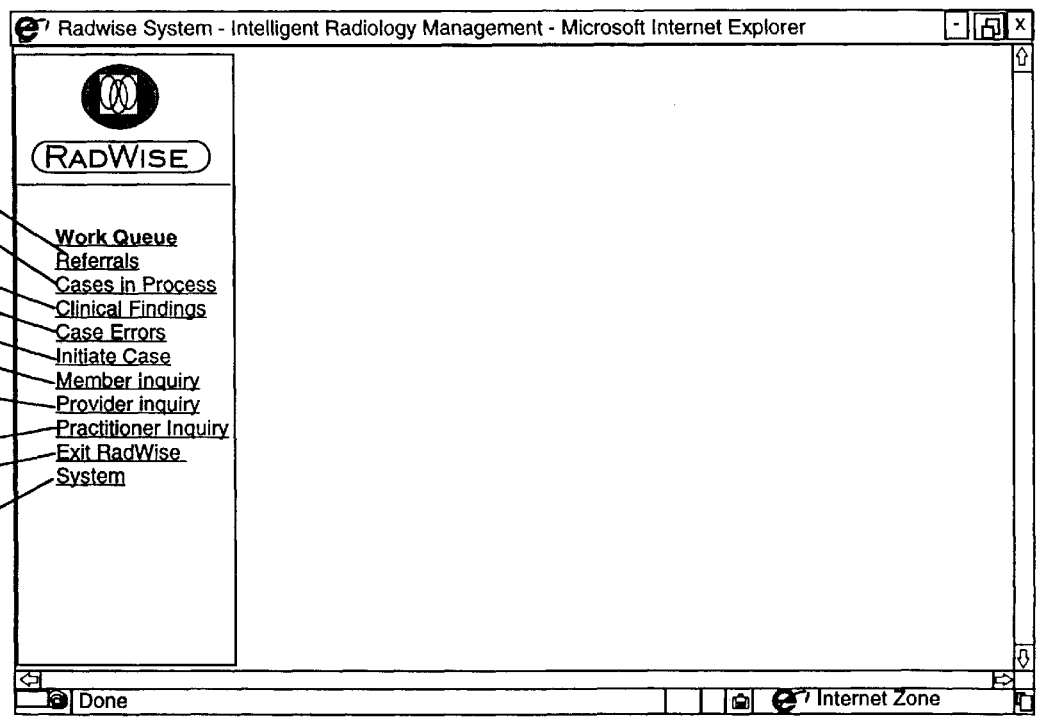

FIG. 9 shows a work queue page. Note that the right portion of the screen remains blank until a hypertext option is chosen. The depicted options include Referrals 409, Cases in Process 411, Clinical Findings 413, Case Errors 415, Case Archives 417, Initiate Case 419, Member Inquiry 421, Provider Inquiry 423, Practitioner Inquiry 425, and Exit RadWise System 429. For purposes of this example, assume that Member Inquiry 421 is selected by the user. This option is selected to create a new case for an existing member. Conversely, Initiate Case 419 would be selected for the creation of a case for a new member.

Figure 10:
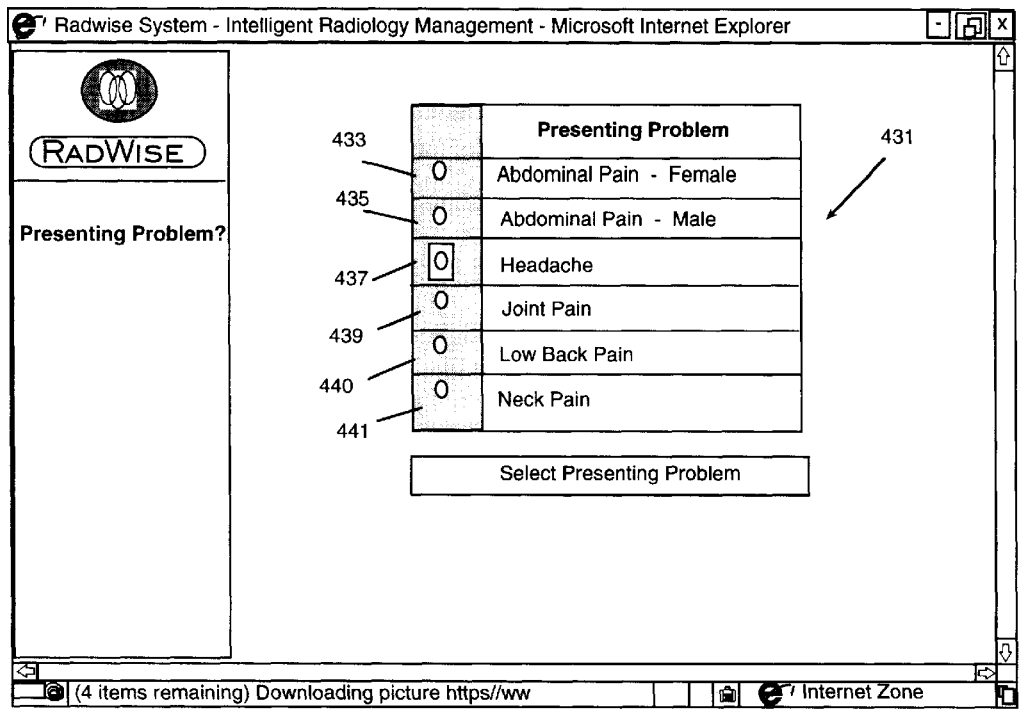

FIG. 10 shows the next appearing screen. This screen displays a list of presenting problems 431—one of which is to be selected by a user. In the depicted embodiment, the list includes abdominal pain (female) 433, abdominal pain (male) 435, headache 437, joint pain 439, low back pain 440, and neck pain 441. This screen corresponds to the "presenting problem" step 210 of routine 200. In this example, as can be seen at 437, the user selected the "headache" option.

Figure 11:
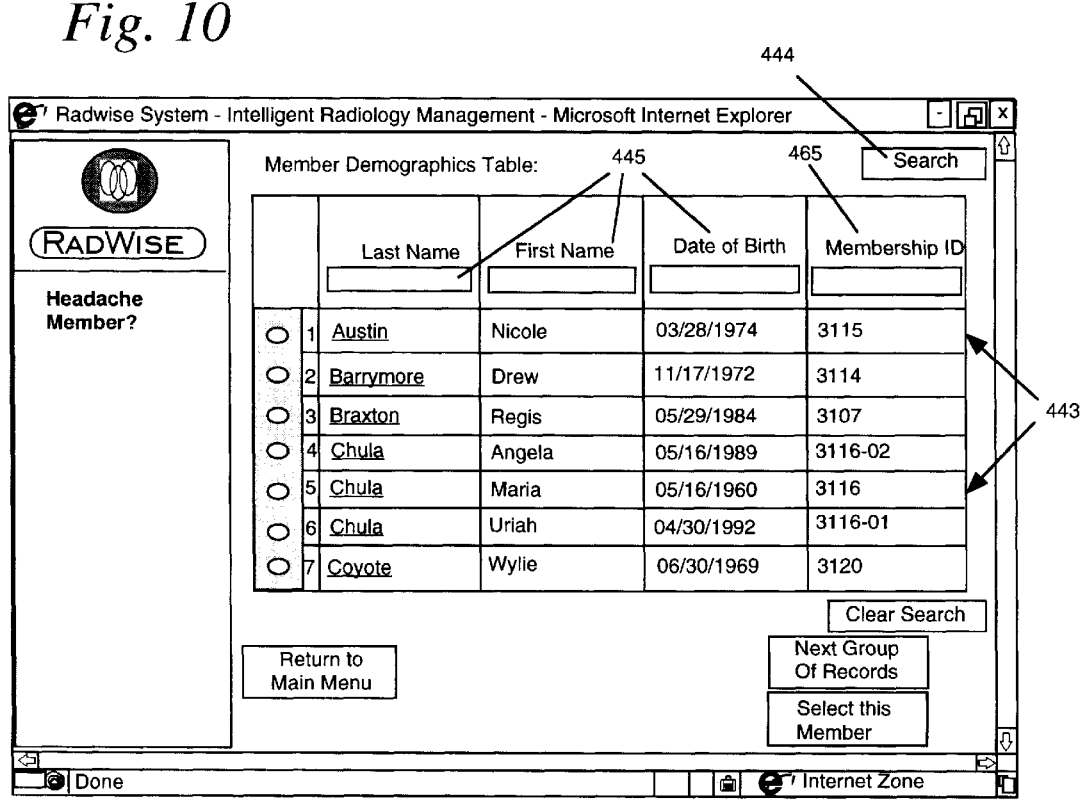

FIG. 11 shows the next screen, which is the beginning of the patient data collection step 220 of routine 200. This particular page includes a Member (e.g., patient) Demographics Table 443 from which a user selects an existing patient record. A patient record is selected by either entering appropriate text into a search field 445 or pressing search button 444, or simply by highlighting an identified patient cell from table 443 and pressing search button 444. The user may also update patient demographics from this table. Assume for this example that a patient named "Tracy P. Nelson" is selected.

Figure 12:
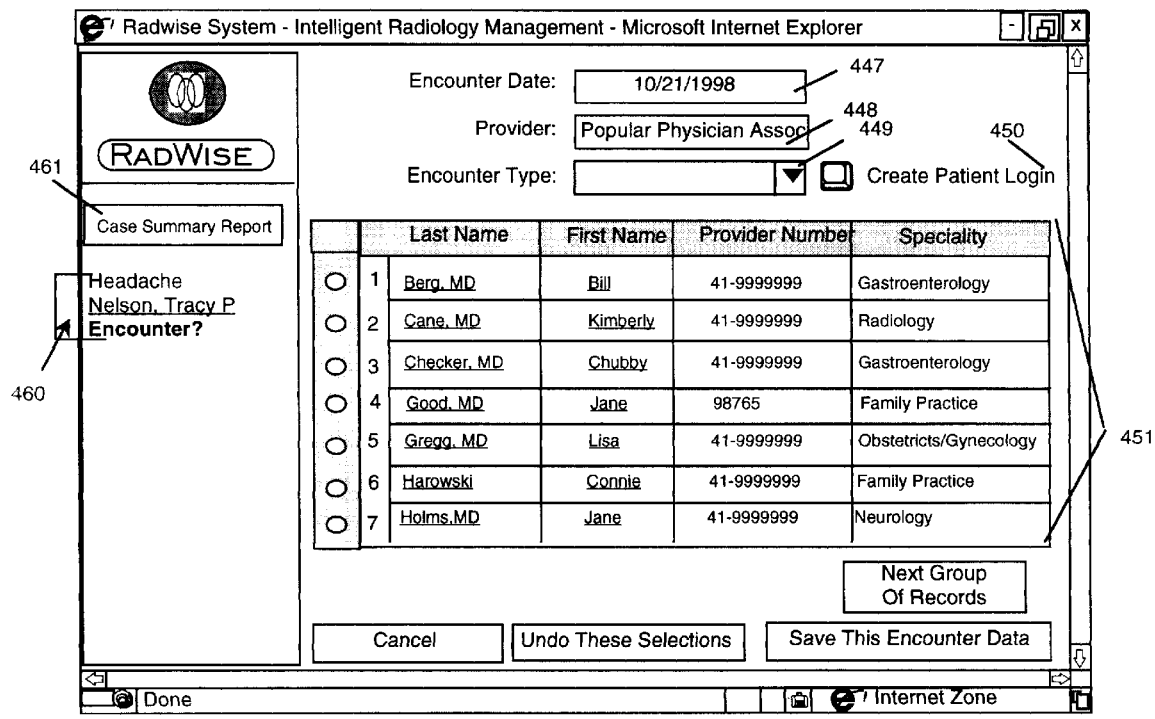

FIG. 12 shows the Physician Encounter page. This page elicits information from a user relating to the patient's encounter with a user, e.g., the primary care physician. The encounter date is entered at 447; the provider is entered at 448; the encounter type (e.g., primary care physician, specialist) is entered at 449; and the particular physician is selected (or entered) at table 451. This screen also includes a Create Patient Login option 450. Create Patient Login option 450 creates a login for a patient to enter information about his/her symptoms through a patient questionnaire. The questionnaire can be filled out at any Internet access point. Note that a running tabulation of some of the already-entered, pertinent data is displayed on the left side of the screen in a case recap field at 460. A "Case Summary Report" link 461 enables a user to display entered data for a selected (highlighted) "encounter?" on the screen. FIG. 29, which will be addressed later, depicts the screen when the "Case Summary Report" link is selected.

Figure 13:
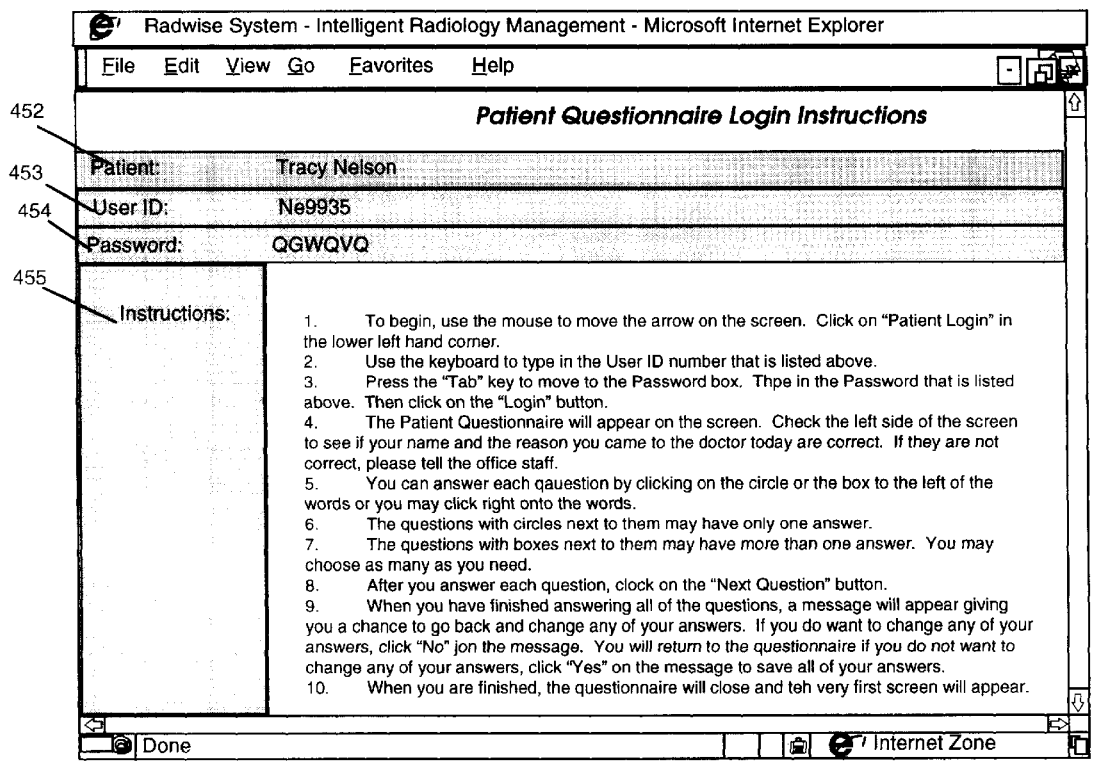
Figure 14:
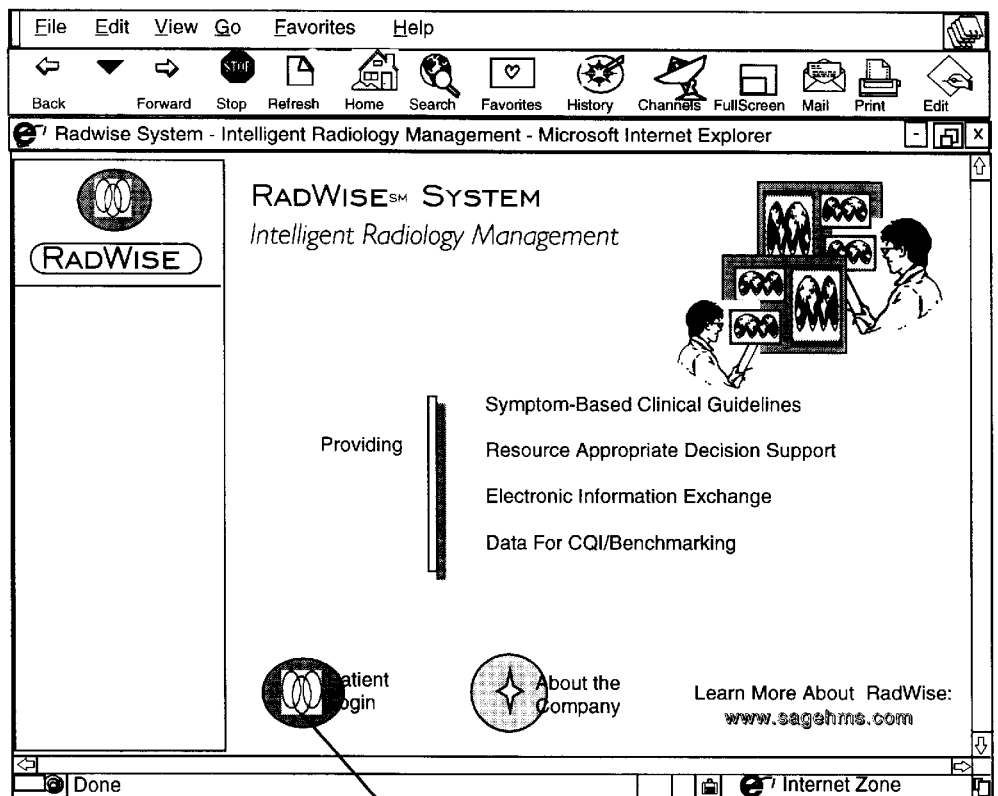
Figure 15:
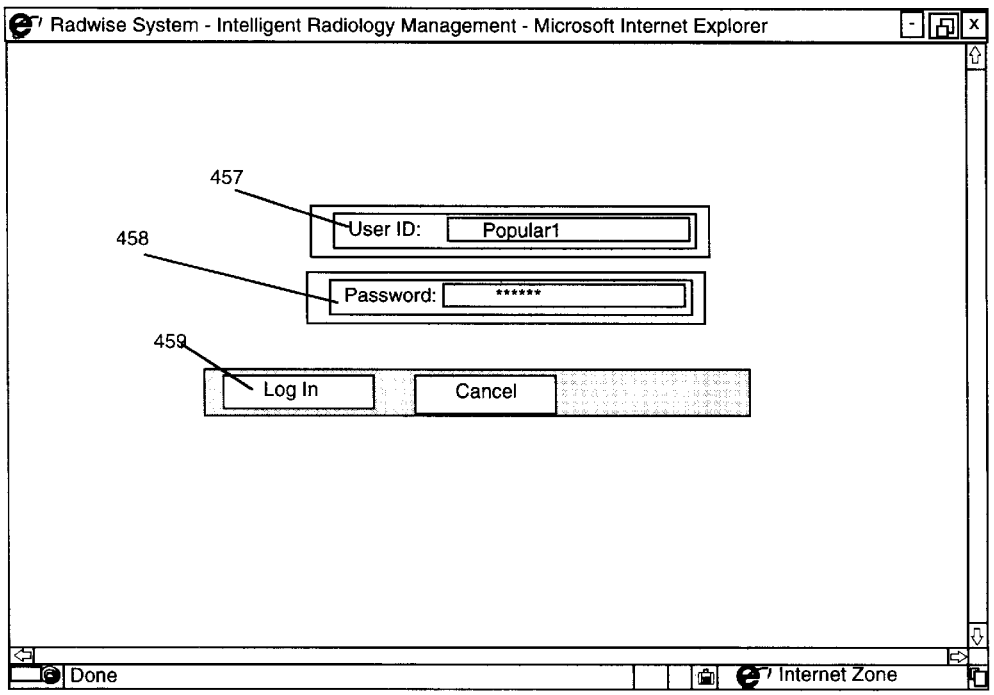

FIG. 13 shows the patient questionnaire which appears as a result of the Create Patient Login option 450 having been selected. It provides the patient's name at 452, a User ID at 453, and PassWord at 454 which allow the patient to enter the RadWise system and fill out the patient questionnaire. The instructions for performing this function are listed at 455. FIG. 14 shows the patient login screen at the time the patient is ready to login and fill out the patient questionnaire. Upon selection of Patient Login at 456, the screen of FIG. 15 appears. At this screen, FIG. 15, the patient enters the previously generated User ID 453 in User ID field 457 and previously generated PassWord 454 at PassWord field 458. The patient then selects the Login Button 459 and completes the questionnaire which is shown in FIG. 16.

Figure 16:
Figure 17:
Figure 18:
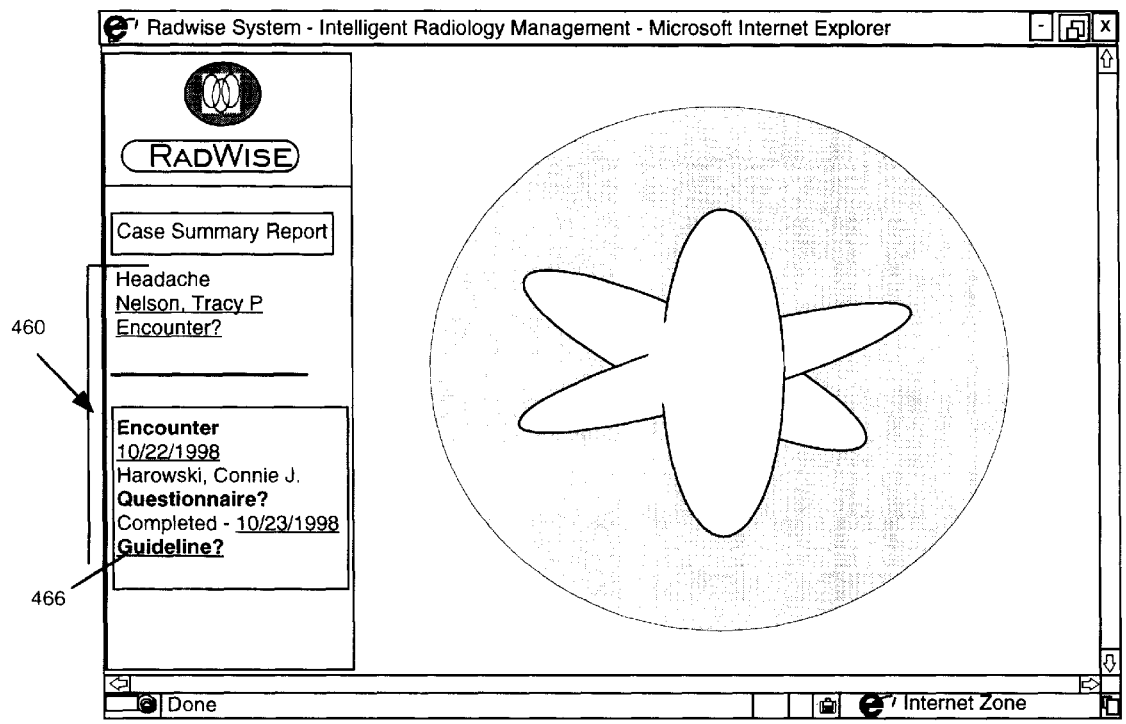

FIG. 16 shows the first page (question) of the patient questionnaire that corresponds to the "headache" presenting problem. This questionnaire is designed to be simple enough to be completed by the patient or by clinical support staff working with the patient. FIG. 17 shows the last page of this 19-question patient questionnaire. FIG. 18 shows the screen after the questionnaire has been completed. Note that the Case Recap field 460, at the left side of the page, indicates that the questionnaire has been completed. At this point, the user selects "Guideline" at 466 to proceed with the program. Here, the user will normally be the physician identified in the previously defined Encounter who will collect and enter into the system physical examination data from the patient.

Figure 19:
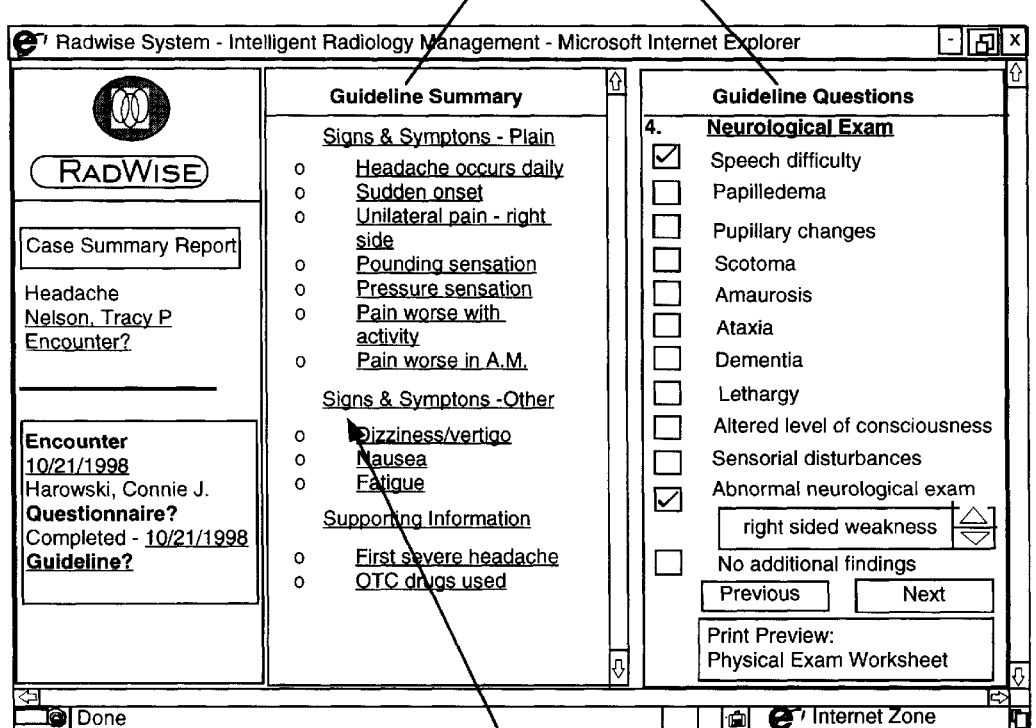
Figure 20:
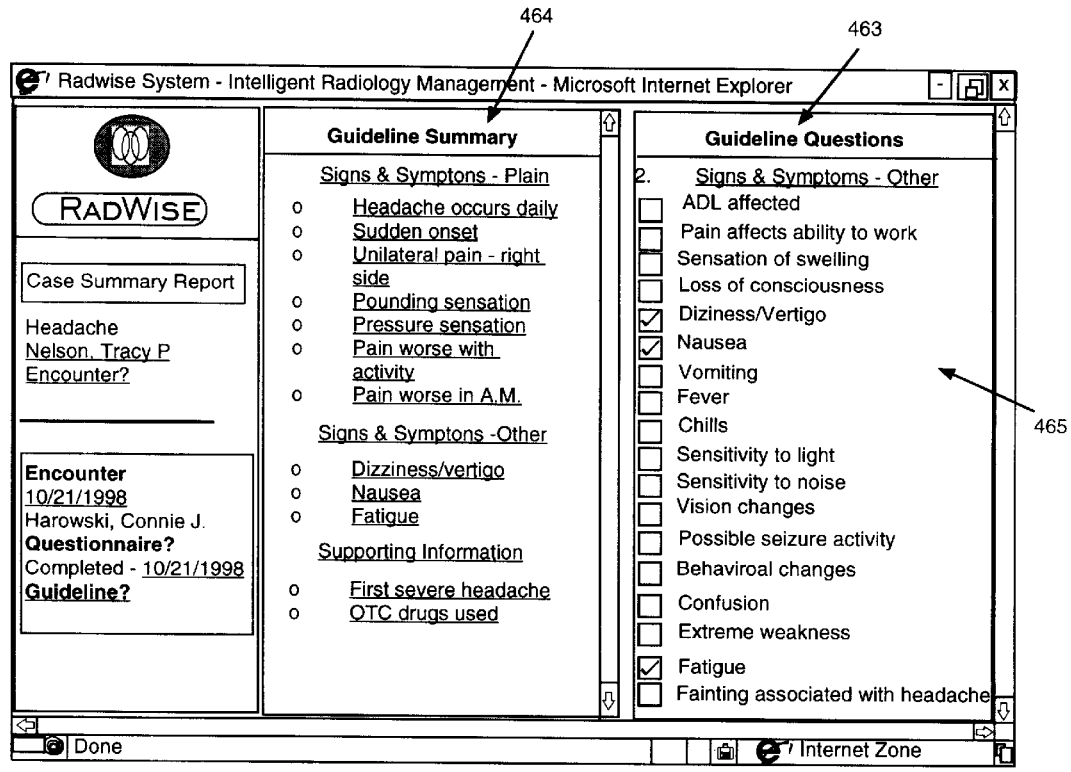

FIG. 19 shows the next page. It includes an updated, Guideline Summary 464, which shows the patient data already collected. The Guideline Questions field 463 displays questions to be completed by the examining physician. Data from these questions will continue to collect in the center of this screen in the Guideline Summary 464. With the system of the depicted embodiment, if the physician has any doubts or concerns regarding the accuracy of the previously answered questions, she may select the appropriate hypertext caption under the Guideline Summary 464 to review the particular questions. For example, if the user selects "Signs & Symptoms—Other" at 462, the screen of FIG. 20 appears and displays the corresponding questions 465 under the Guideline Questions at 463.

Figure 21:
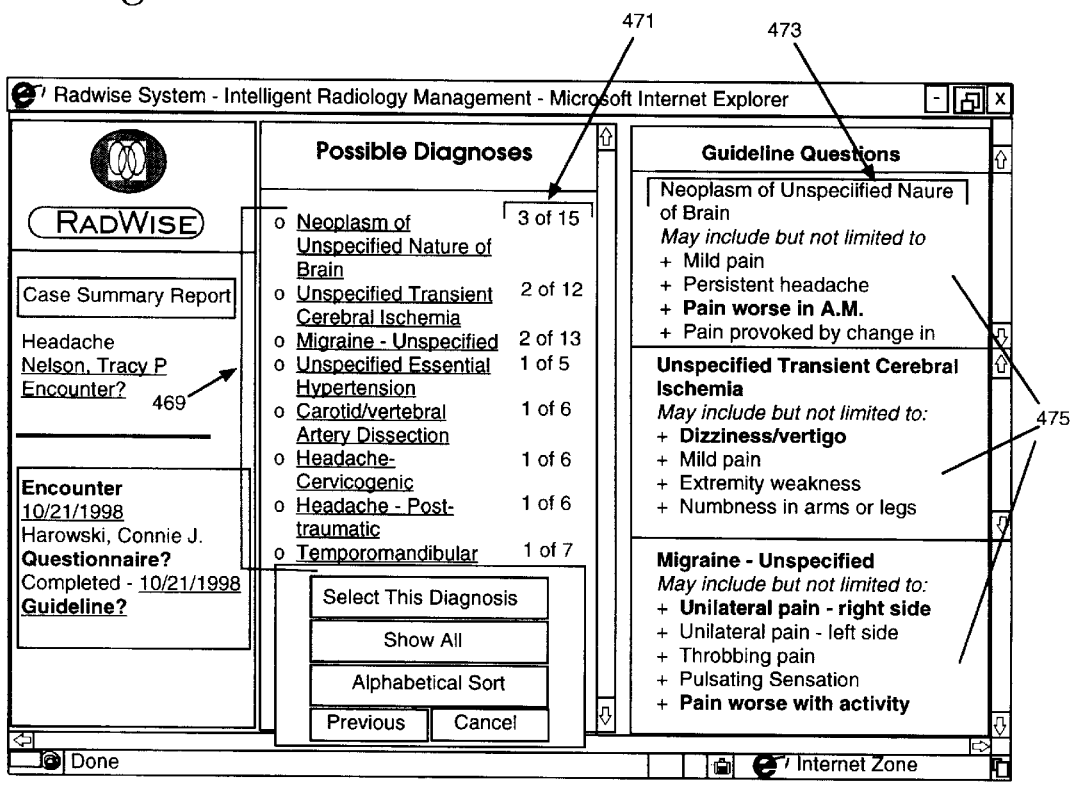

FIG. 21 shows the next screen, which displays the list of Possible Diagnoses 469. This page corresponds to step 230 in routine 200. Symptom hit data for each diagnosis within this list appears in Column 471. This symptom hit data is presented in a "n" of "m" format, where "m" represents all of the symptoms associated with the listed diagnosis from the guidelines and "n" represents those symptoms associated with the selected patient given the inputs from the patient questionnaire, neurological exam, and physical exam. The right side 473 of the screen includes fields 475 that each provide detailed symptomatic data for requested possible diagnoses. This detailed data, along with the symptom hit data 471, corresponds to the "additional details" provided in steps 235 and 237 of routine 230. Within each field 475, a requested diagnosis is identified and its associated guideline signs and symptoms are listed. The signs and symptoms that are obtained from the patient are highlighted as symptom hits. In this manner, a user can readily analyze this additional symptomatic information by simply clicking on a diagnosis and scrolling through its field 475 to review the associated symptoms, along with the symptom hits for this particular patient.

FIG. 22 shows the next screen, which provides the recommended diagnostic task, which corresponds to step 250 in routine 200. Upon selecting a possible diagnosis, a "Recommendation" screen appears. The user can choose to accept the system recommendation task at 476 or create a different service record (self-defined task) at 478. In this example, the recommended diagnostic task is an MRI of the brain.

Figure 22B:
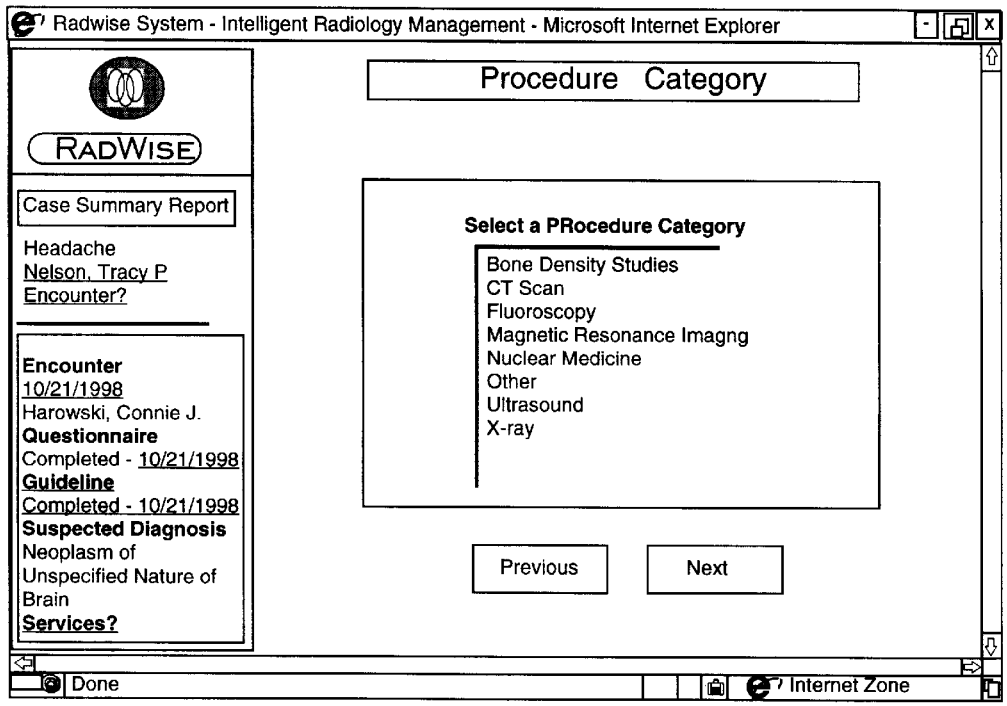
Figure 22C:
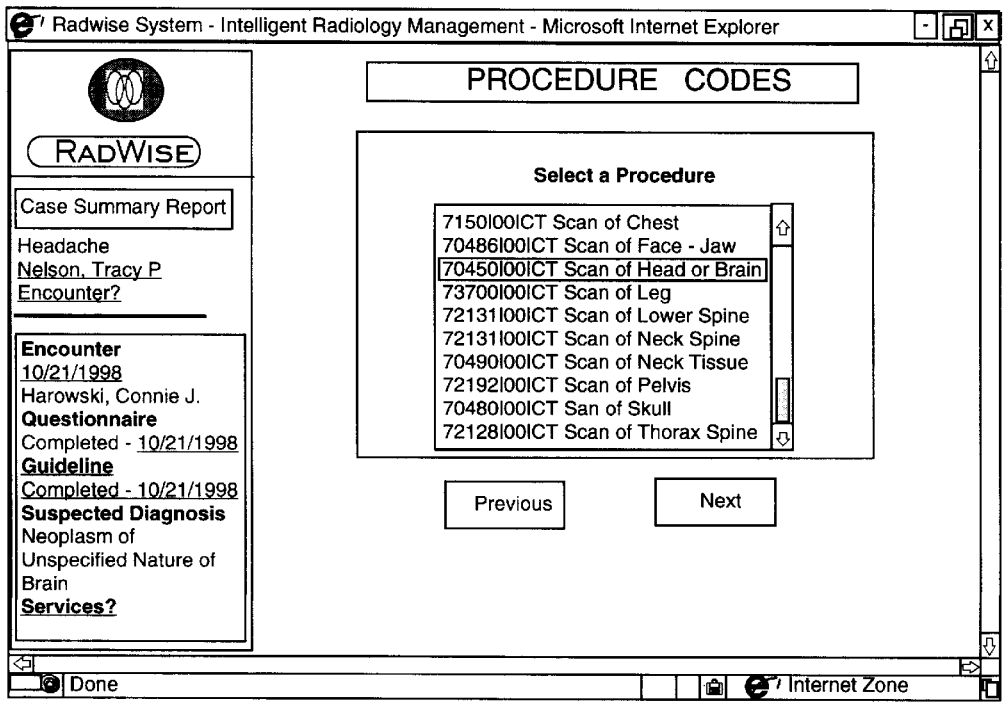
Figure 22D:
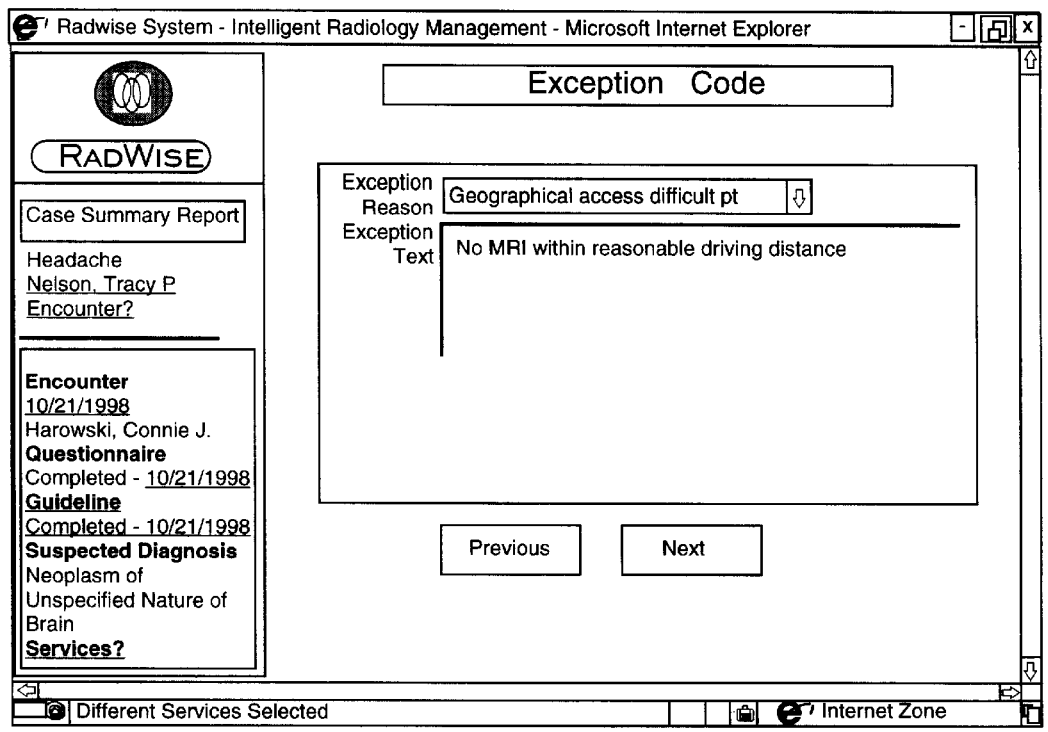
Figure 23:
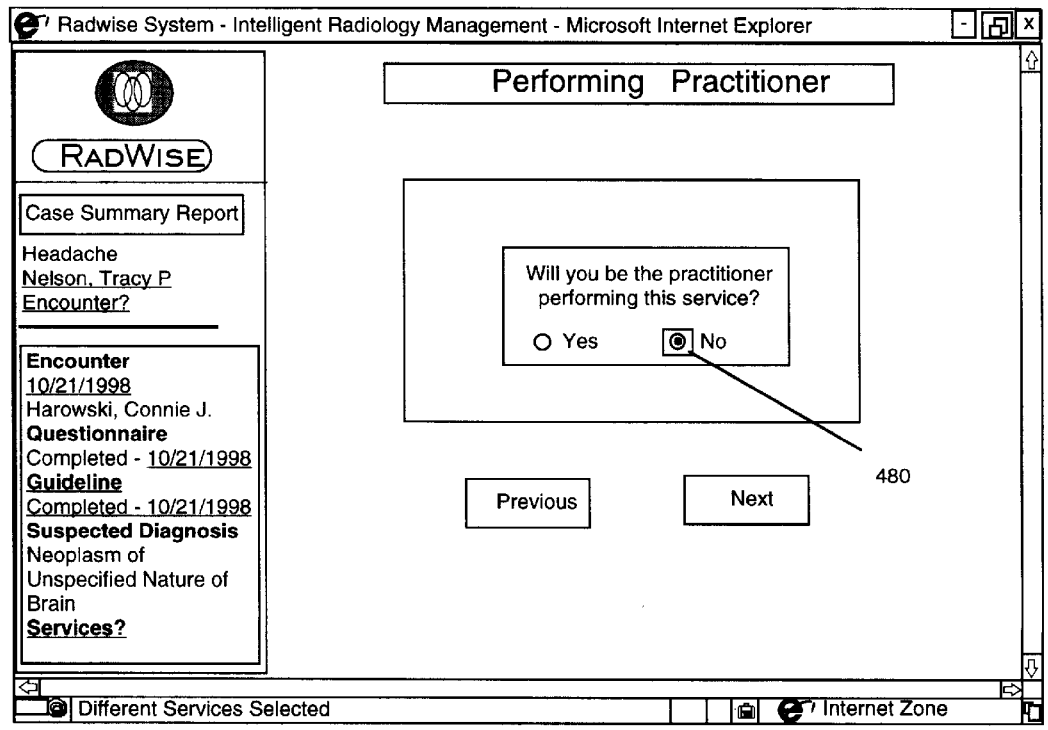

Assume that the user chooses to reject the presented recommendation. The user would then select the button Create Different Service Record 478 and the screen of FIG. 22A would appear. This screen is a "Service Type" screen; it enables the user to select a different task other than the recommended diagnostic task. From here, the next appearing screens are the "Procedure Category" and "Procedure Code" screens, respectively, which are shown in FIGS. 22B and 22C. These screens allow the user to define a more particular procedure within the previously selected Service type. The next screen, which is shown in FIG. 22D, is the "Exception Code" screen. This screen elicits, from the user, his/her reasons as to why the recommended diagnostic task was rejected.

Now, assume that the user had accepted the recommended diagnostic task (by selecting button 476) at the screen of FIG. 22. The screen of FIG. 23 would next appear. This "Performing Practitioner" screen initiates the posting of this task, which corresponds to step 290 of routine 200. In this case, posting is achieved through the generation of a service record, which begins with the user (e.g., primary care physician) specifying who should perform the diagnostic task. Initially, with this screen, the user is asked if he/she will be performing the service. For this example, the user has responded "no" at 480 to this question.

Next, in FIG. 24, the system then elicits the particular service provider. In this case, a particular radiology group is selected for the accepted diagnostic task (performance of the MRI on the patient's brain). FIG. 25 shows the next screen, which enables the user to confirm its posting of the recommended task. In this screen, a summary of the particular requested service and service providers are presented.

At this point, the first user (or users corresponding to the primary care physician) has completed the initial portion of interacting with the system. The case record (which includes relevant patient history and physical examination data) for Tracy P. Nelson's "headache" encounter has been generated, and the accepted, recommended diagnostic task has been posted, in this case, to be performed by a separate user other than the examining physician. The next phase of diagnosis and interaction with the system will occur with this separate user, i.e. radiology group.

Figures 26, 27:
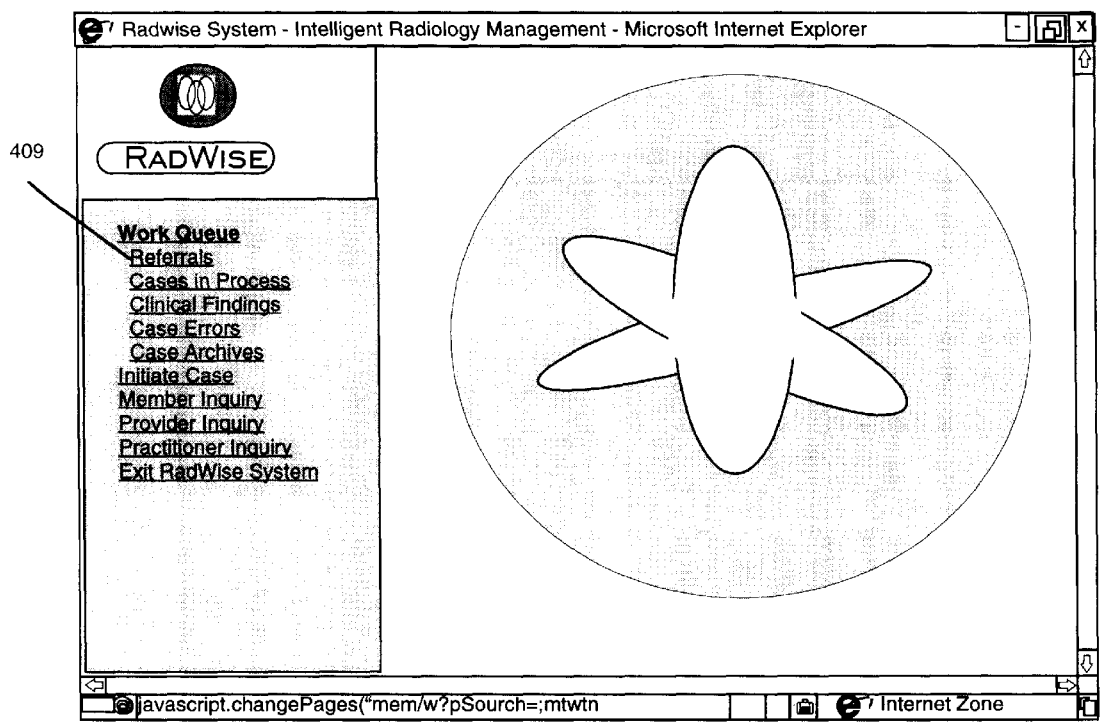

Assume that a user from the radiology group has logged onto the system and is now at the "Work Queue" screen, which is shown in FIG. 26. This is the same screen that appeared before in FIG. 9 for the first user; however, this time, the user (i.e., radiologist) will select Referrals 409. FIG. 27 shows the next screen, which is the "Work Queue- Referrals" screen. This screen includes a table 479 of patient records for patients who have been provided 20 by notice to this radiology group (i.e., "Radical Radiologists"). Table 479 includes a column of patient names 481, which as can be seen includes our exemplary patient: Tracy P. Nelson at 483. With the selection of Ms. Nelson, a radiologist encounter page (FIG. 28) appears for the selection of a particular radiologist responsible for performing the procedure. In this example, "Randy Tesla" is being selected as the performing radiologist, as can be seen at 482. This encounter page also includes a Create Patient Login option 484, which operates similarly to the Create Patient Login option of FIG. 12. This option 484, when selected, enables the patient to login to the system and complete a patient questionnaire relating to his or her upcoming radiological examination.

Figure 30:
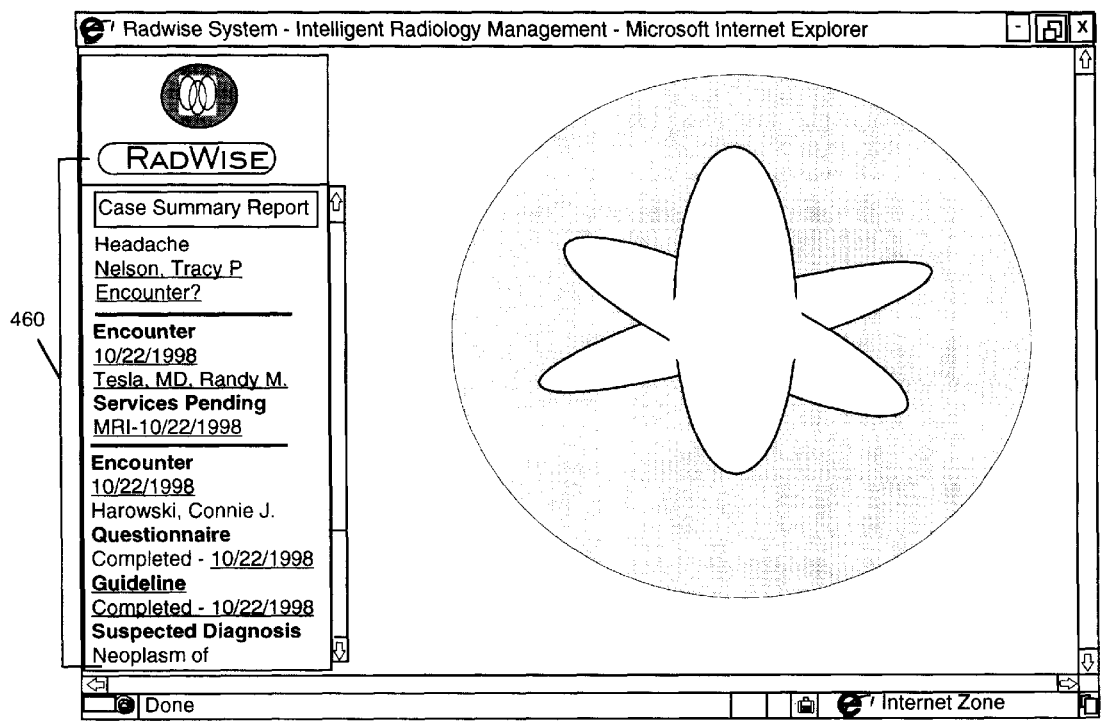

At this point, the radiology group has chosen a particular radiologist, Randy Tesla, to perform the MRI task. FIG. 29 shows the work queue screen once again; this time, however, it is being accessed by Mr. Tesla, and he selects Cases In Process 486 in connection with performing the task. As may be apparent from the name, this option enables a user to review previously-generated cases that have not yet been completed. Here, Mr. Tesla selects Tracy P. Nelson at 485. FIG. 30 shows the screen that appears when "Tracy P. Nelson" has been selected. This screen shows what has been done and what is pending in Case Recap field 460 on the left side of the page.

Figure 31:
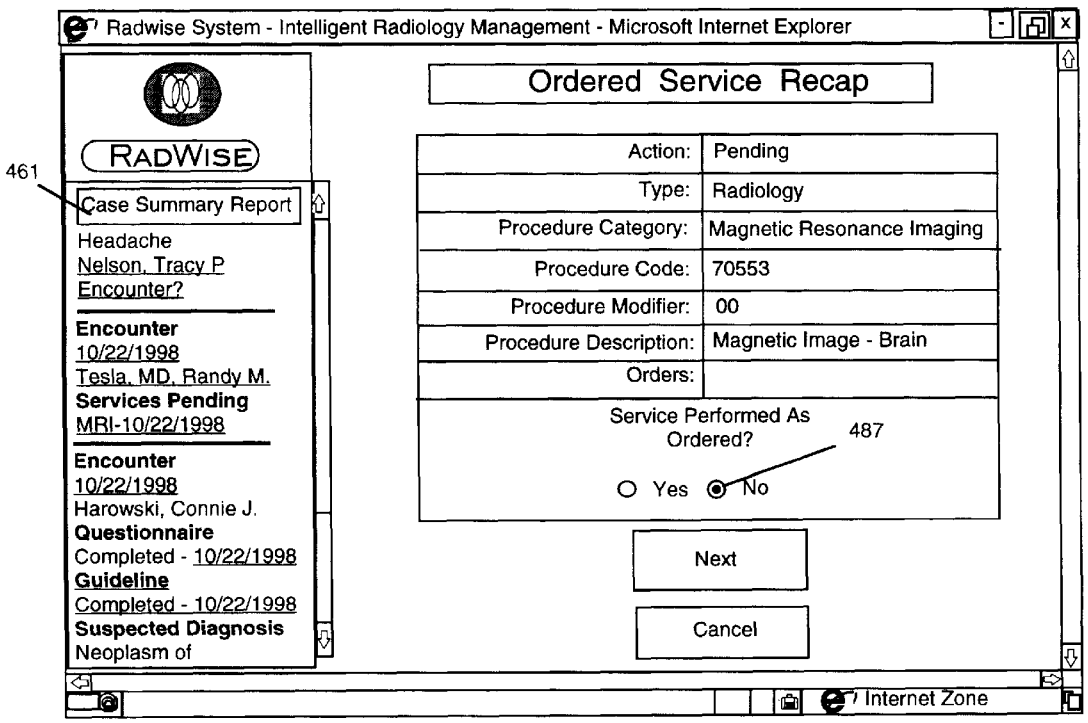
Figure 32:
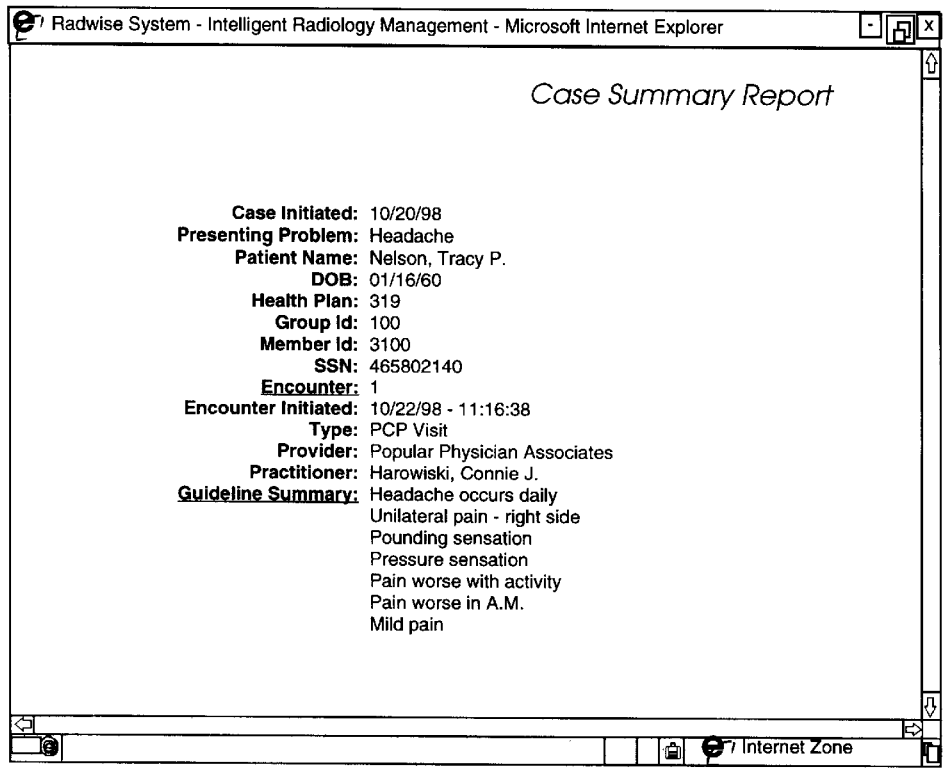

FIG. 31 shows the next appearing screen, which is the "Ordered Service Recap" screen. This screen summarizes the ordered service for Mr. Tesla and prompts him to specify whether or not he will perform the task as ordered. In this case, at 487 he indicates that he will not be performing the service in the specified manner. Selecting case summary report 461 at the screen of FIG. 31 allows a case summary report to be seen on the screen as described in FIG. 32. FIG. 32 shows the next screen, which shows the "Case Summary Report". This screen provides the task provider, Mr. Tesla, with on-line access to the previously obtained, relevant patient data. This is beneficial because it obviates the need to contact the initial examining physician for this information.

Figure 33:
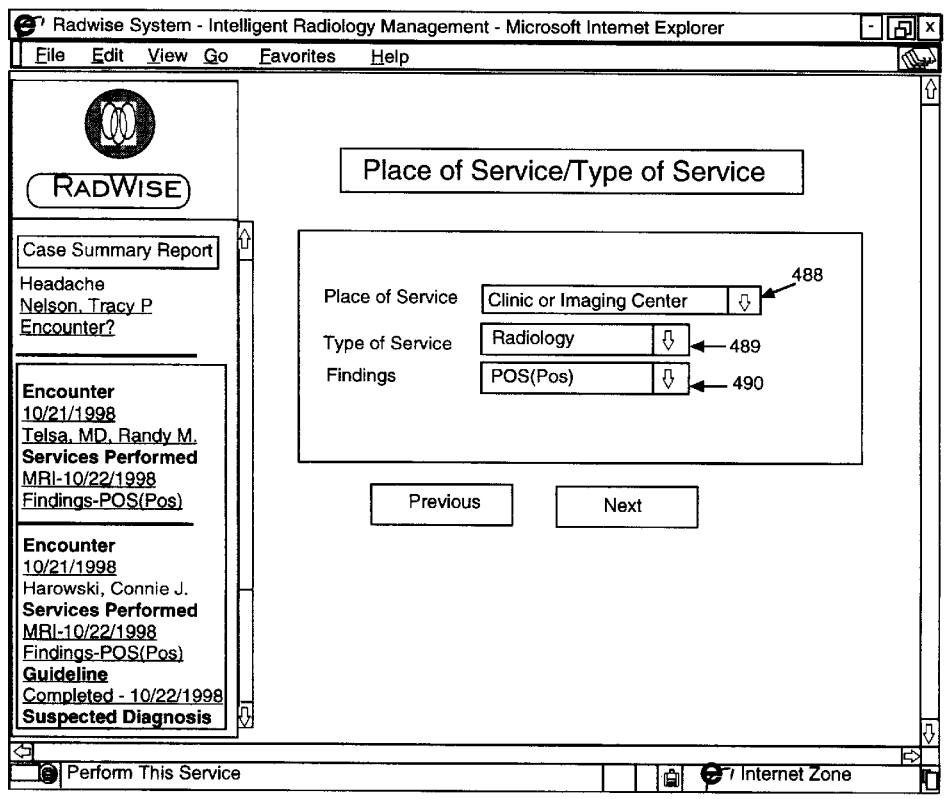

FIG. 33 shows the "Place of Service/Type of Service" screen. In this screen, the task performer (in this case, radiologist, Randy Tesla) indicates the place, type, and results of the service. The place of service is entered at 488 and the type of service is entered at 489. A two variable, boolean-type code, which is used to efficiently convey the findings, is entered into field 490. The first variable of this code indicates whether or not a pathology was detected, and the second variable of this code indicates whether the findings related to the suspected (i.e., selected) diagnosis. The possible outcomes are positive/positive (suspected diagnosis confirmed), positive/negative (pathology detected but not suspected diagnosis), negative/positive (no pathology detected but something related to suspected diagnosis or other condition was observed), negative/negative (no pathology detected and nothing observed relating to the suspected diagnosis), and equivocal (findings uncertain). In this example, the task performer entered positive/positive at 490, which indicates that the suspected diagnosis: Neoplasm of Unspecified Nature of Brain, was confirmed.

Figure 34:
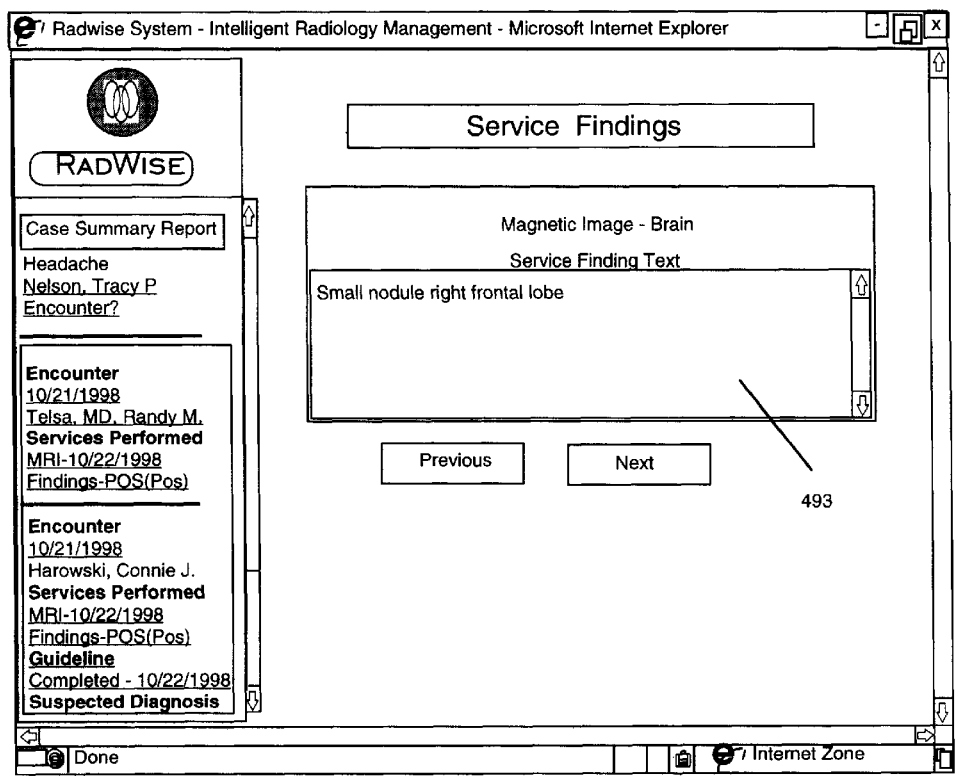

FIG. 34 shows the "Service Findings" screen, which includes a Service Findings Text field 493 for enabling the task (service) performer to elaborate on the findings.

Figure 35:
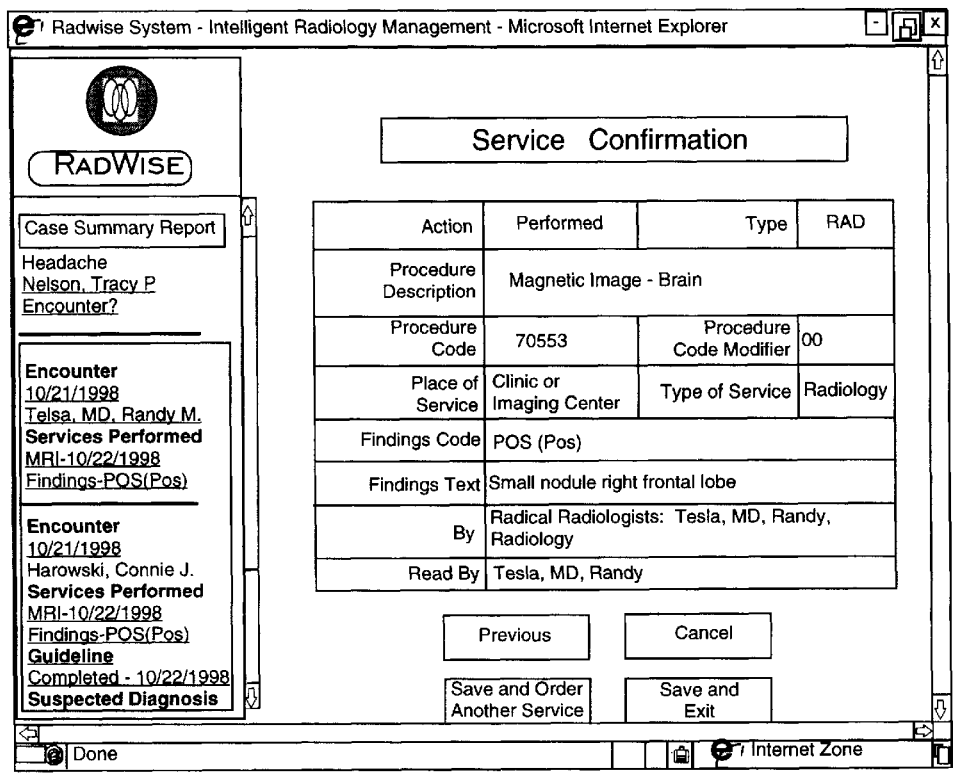

FIG. 35 shows the "Service Confirmation" screen, which enables the task performer to review his/her findings and data before entering them into the system.

Figure 36:
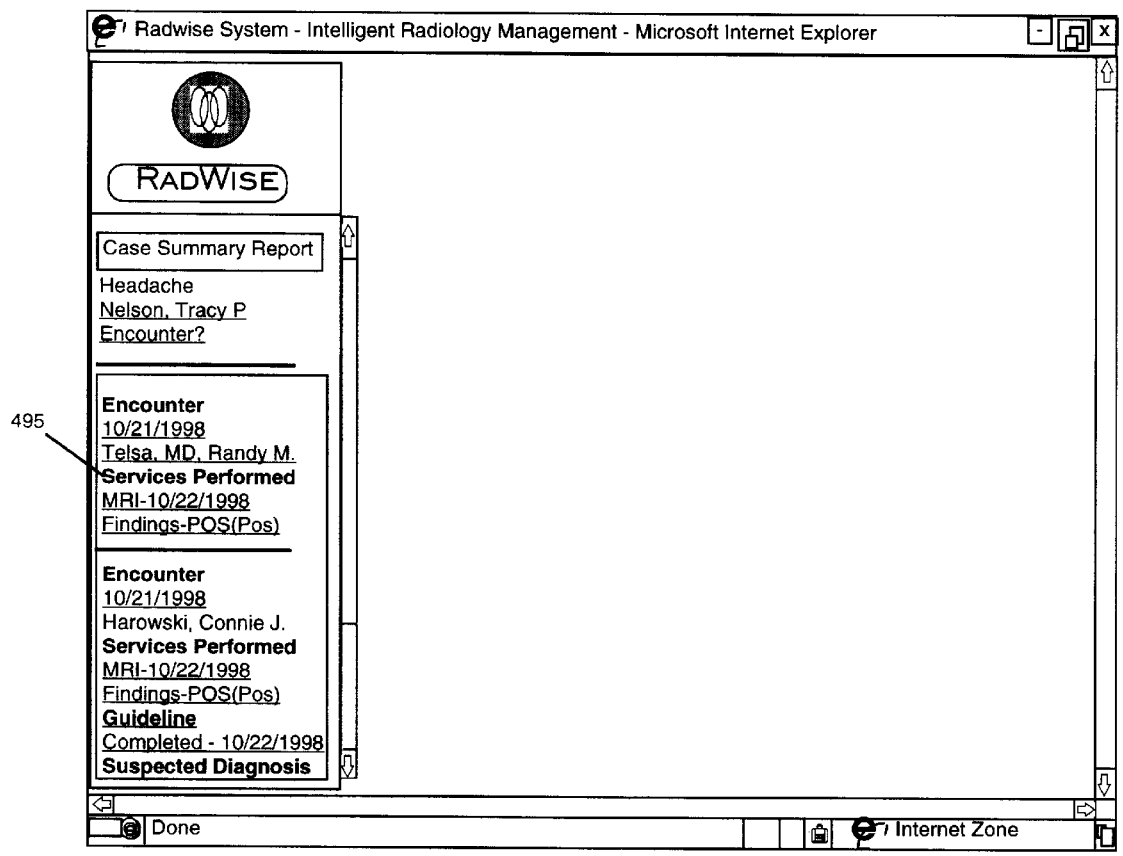

Once service confirmation has been entered, the "Recap Menu" screen, which is the next screen as shown in FIG. 36, indicates at 495 that the service (i.e., diagnostic task) was performed.

5.4 Other Embodiments

While the present invention has been primarily described with reference to one embodiment thereof, those skilled in the art will recognize various changes that may be made without departing from the spirit and scope of the claimed invention.

For example, while the diagnostic enhancement program has primarily been discussed as being operated within a server, it is contemplated that the program could also be effectively executed with a personal computer, a mainframe computer, or even in a dedicated processor-based system.

Accordingly, the invention is not limited to what is expressly shown in the drawings and described in the specification.

What is claimed is:

1. A method for selecting a diagnostic task for a patient, comprising:
   (a) receiving for a patient a presenting problem and related data points involving a patient history and a physical examination for the patient;
   (b) selecting and presenting a guideline-based data collection procedure based upon the presenting problem. and the data points, and receiving acquired data on the patient as a result of the procedure;
   (c) providing for display a plurality of possible diagnoses, for selection by a first user, based on criteria applied to the acquired data on the patient;
   (d) receiving a selection of a possible diagnosis from the plurality of displayed possible diagnoses; and
   (e) presenting an appropriate recommended diagnostic task for the patient based on the selected possible diagnosis and a cost-effectiveness of the diagnostic task as related to the selected possible diagnosis for use in acquiring additional data related to the possible diagnosis.

2. The method of claim 1, wherein the method further includes the act of posting the appropriate recommended diagnostic task if accepted by the first user.

3. The method of claim 1, wherein the step of providing for display includes providing at least one possible diagnosis based on the presenting problem and the acquired patient data.

4. The method of claim 3, wherein the acquired patient data include symptoms that relate to the presenting problem.

5. The method of claim 1, wherein the step of providing for display includes the act of conveying to the first user information on a relationship between the acquired data and the at least one possible diagnosis.

6. The method of claim 1, wherein the step of providing for display includes the step of making available to the first user additional information.

7. The method of claim 6, wherein the additional information includes a list of associated symptoms.

8. The method of claim 7, wherein the additional information further includes indicating for a requested possible diagnosis the associated symptoms that are reported in the acquired data on a patient.

9. The method of claim 8, wherein the method further includes indicating a relative value of a symptom hit for a selected possible diagnosis.

10. The method of claim 1, wherein the method further includes presenting a display for use in selecting the presenting problem.

11. The method of claim 1, wherein the method further includes presenting an on-line questionnaire for use in obtaining the acquired data.

12. The method of claim 1, wherein the method further includes presenting a screen displaying the guideline-based data collection procedure.

13. The method of claim 1, wherein the method further includes presenting a screen for the first user to select the appropriate recommended diagnostic task.

14. The method of claim 1, wherein the method further includes presenting a screen displaying a work queue compiling identification of a plurality of patients and associated presenting problems.

15. The method of claim 1, wherein the method further includes presenting a screen displaying an on-line case summary including an identification of the patient, an identification of the presenting problem, and the acquired patient data.

16. A method for selecting a diagnostic task for a patient comprising:
   (a) receiving for a patient a presenting problem and related data points involving a patient history and a physical examination for the patient;
   (b) selecting and presenting a guideline-based data collection procedure based upon the presenting problem and the data points, and receiving acquired data on the patient as a result of the procedure;
   (c) providing for display at least one possible diagnosis for selection by a first user based on criteria applied to the acquired data on the patient;
   (d) presenting an appropriate recommended diagnostic task for the patient based on the selected possible diagnoses and a cost-effectiveness of the diagnostic task as related to the selected possible diagnoses;
   (e) posting the recommended diagnostic task if accepted by the first user; and
   (f) receiving and storing the results of the posted diagnostic task.

17. The method of claim 16, wherein the results of the posted diagnostic task include indicating whether the selected possible diagnosis is correct.

18. The method of claim 17, wherein the results of the posted diagnostic task further include a status of an alternative diagnosis.

19. A method for selecting a diagnostic task for a patient, comprising:
   (a) receiving for a patient a presenting problem and related data points involving a patient history and a physical examination for the patient;
   (b) selecting and presenting a guideline-based data collection procedure based upon the presenting problem and the data points, and receiving acquired data on the patient as a result of the procedure;
   (c) providing for display at least one possible diagnosis for selection by a first user based on criteria applied to the acquired data on the patient;
   (d) presenting an appropriate recommended diagnostic task for the patient based on the selected possible diagnosis and a cost-effectiveness of the diagnostic task as related to the selected possible diagnosis;
   (e) posting the recommended diagnostic task if accepted by the first user; and
   (f) enabling the first user to self-define a diagnostic task when the first user does not accept the recommended diagnostic task.

20. A computer-based method for diagnosing a patient pathology, comprising:
   (a) identifying for a patient a presenting problem and related data points involving a patient history and a physical examination for the patient;
   (b) selecting and presenting a guideline-based data collection procedure based upon the presenting problem and the data points, and receiving acquired data on the patient as a result of the procedure;
   (c) receiving a selection of a first diagnosis from a list of possible diagnoses, wherein the possible diagnoses are based on the acquired patient data;
   (d) performing an appropriate diagnostic task based on the selected first diagnosis and a cost-effectiveness of the diagnostic task as related to the selected first diagnosis for use in acquiring additional data related to the possible diagnosis, wherein the performed task produces a diagnostic task result; and
   (e) making a second diagnosis based on the diagnostic task result.

21. A method for managing the performance of a diagnostic task, comprising:
   (a) receiving from a first user a selected possible diagnosis for a patient;
   (b) providing the first user with an appropriate recommended diagnostic task for use in acquiring additional data related to the possible diagnosis, wherein the appropriate recommended diagnostic task is selected based upon the selected possible diagnosis, data points involving a patient history and a physical examination for the patient, and a cost-effectiveness of the diagnostic task as related to the selected possible diagnosis;
   (c) enabling a second user to perform the task if accepted by the first user; and
   (d) enabling a self-defined task to be performed if the recommended task is not accepted by the first user.

* * * * *